United States Patent [19]
Haxo, Jr. et al.

[11] Patent Number: 6,143,252
[45] Date of Patent: Nov. 7, 2000

[54] PIPETTING DEVICE WITH PIPETTE TIP FOR SOLID PHASE REACTIONS

[75] Inventors: Francis Theodore Haxo, Jr., San Francisco; Liang Boon Hoe, Sunnyvale, both of Calif.

[73] Assignee: The Perkin-Elmer Corporation, Foster City, Calif.

[21] Appl. No.: 09/292,777

[22] Filed: Apr. 12, 1999

[51] Int. Cl.[7] ...................................................... B01L 3/02
[52] U.S. Cl. .......................... 422/131; 422/63; 422/100; 422/923; 73/863.32; 73/864.16; 73/864.17
[58] Field of Search ........................... 73/863.31–863.33, 73/864.87, 864.16, 864.17; 422/63, 100, 135, 134, 131, 923; 436/180; 128/DIG. 1

[56] References Cited

U.S. PATENT DOCUMENTS

| | | |
|---|---|---|
| 3,568,735 | 3/1971 | Lancaster . |
| 3,590,889 | 7/1971 | Vannus . |
| 3,831,601 | 8/1974 | Kessell . |

(List continued on next page.)

FOREIGN PATENT DOCUMENTS

| | | |
|---|---|---|
| 0 344 177 B1 | 5/1994 | European Pat. Off. . |
| H4-15019 | 3/1992 | Japan . |
| WO 97/26539 | 7/1997 | WIPO . |
| WO 97/26540 | 7/1997 | WIPO . |
| WO 98/35753 | 8/1998 | WIPO . |

OTHER PUBLICATIONS

Lashkari, D.A., et al., "An Automated Multiplex Oligonucleotide Synthesizer: Development of High–Throughput, Low–Cost DNA Synthesis," *Proc. Natl. Acad. Sci. USA* 92:7912–7915 (1995).

Oste, C.C., "Optimized DNA Synthesis Methods on the Oligo 1000M DNA Synthesizer," Beckman Instruments, Fullerton, CA (1996) (company manual).

Schreuer, O., et al., "Development of an Automated System for the Multiple Parallel Production of Synthetic Oligonucleotides," Fifth International Symposium on Solid Phase Synthesis & Combinatorial Chemical Libraries, London, England, (1997) (poster).

Sindelar, L.E., and Jaklevic, J.M., "High–Throughput DNA Synthesis in a Multichannel Format," *Nuc. Acids Research* 23(6):982–987 (1995).

Wilson, R.K., et al., "Automation of Dideoxynucleotide DNA Sequencing Reactions Using a Robotic Workstation," *BioTechniques* 6(8):776 (1988).

Declaration Under 37 CFR 1.131 by J.B. Rampal and J.F. Harbaugh with Exhibit pp. A1–A9 and B1–B2 from USPTO file history of Patent No. 5,437,979, as apparently received by the USPTO on Sep. 24, 1994.

*Primary Examiner*—Jacqueline V. Howard
*Assistant Examiner*—Susan Ohorodnik
*Attorney, Agent, or Firm*—John Brady

[57] ABSTRACT

A pipetting device for use with a pipette tip containing a solid phase reaction support, comprising a cylinder, a plunger movable within the cylinder between a retracted and an extended position, and a seal disposed between the plunger and cylinder for holding the plunger as it moves. The plunger has a central passageway within an upper portion of the plunger communicating with a side egress port on the plunger, the plunger movable between a retracted position, for aspirating and dispensing liquid reagent wherein the port remains above the seal, and an inserted position wherein the port is positioned below the seal for allowing fluid (e.g., washing solution or inert gas) to be introduced into the cylinder and tip. In an apparatus and method, an array of such devices is used, each fitted with a pipette tip having a solid support retained therein, for performing high-throughput and parallel chemical synthesis of biopolymers (e.g., oligonucleotides or peptides). In one aspect, means are provided for separately controlling the movement of each device in the apparatus for contacting liquid reagent with the solid support. In another aspect, a tip remover is provided for selectively removing tips containing completed polymer.

10 Claims, 18 Drawing Sheets

U.S. PATENT DOCUMENTS

| | | |
|---|---|---|
| 3,853,011 | 12/1974 | Baumann . |
| 4,008,736 | 2/1977 | Wittmann-Liebold et al. . |
| 4,036,064 | 7/1977 | Hydo . |
| 4,047,438 | 9/1977 | Sekine . |
| 4,087,248 | 5/1978 | Miles . |
| 4,106,911 | 8/1978 | Marcelli . |
| 4,144,761 | 3/1979 | Dzaack . |
| 4,215,092 | 7/1980 | Suovaniemi et al. . |
| 4,228,831 | 10/1980 | Kerns . |
| 4,255,096 | 3/1981 | Coker, Jr. et al. . |
| 4,335,621 | 6/1982 | Tervamäki et al. . |
| 4,353,989 | 10/1982 | Bender et al. . |
| 4,407,659 | 10/1983 | Adam . |
| 4,458,066 | 7/1984 | Caruthers et al. . |
| 4,470,317 | 9/1984 | Sabloewski et al. . |
| 4,483,964 | 11/1984 | Urdea et al. . |
| 4,500,707 | 2/1985 | Caruthers et al. . |
| 4,511,534 | 4/1985 | Bennett et al. . |
| 4,517,338 | 5/1985 | Urdea et al. . |
| 4,532,805 | 8/1985 | Flesher . |
| 4,554,839 | 11/1985 | Hewett et al. . |
| 4,598,049 | 7/1986 | Zelinka et al. . |
| 4,624,659 | 11/1986 | Goldberg et al. . |
| 4,671,941 | 6/1987 | Niina et al. . |
| 4,689,405 | 8/1987 | Frank et al. . |
| 4,728,502 | 3/1988 | Hamill . |
| 4,748,859 | 6/1988 | Magnussen, Jr. et al. . |
| 4,763,535 | 8/1988 | Rainin et al. . |
| 4,794,085 | 12/1988 | Jessop et al. . |
| 4,827,780 | 5/1989 | Sarrine et al. . |
| 4,846,797 | 7/1989 | Howson et al. ............ 604/154 |
| 5,026,773 | 6/1991 | Steel . |
| 5,047,524 | 9/1991 | Andrus et al. . |
| 5,053,454 | 10/1991 | Judd . |
| 5,055,263 | 10/1991 | Meltzer . |
| 5,100,805 | 3/1992 | Ziege et al. . |
| 5,104,621 | 4/1992 | Pfost et al. . |
| 5,112,575 | 5/1992 | Whitehouse et al. . |
| 5,132,418 | 7/1992 | Caruthers et al. . |
| 5,171,537 | 12/1992 | Wainwright et al. . |
| 5,175,209 | 12/1992 | Beattie et al. . |
| 5,273,718 | 12/1993 | Sköld et al. . |
| 5,288,468 | 2/1994 | Church et al. . |
| 5,295,966 | 3/1994 | Stern et al. . |
| 5,306,510 | 4/1994 | Meltzer . |
| 5,336,201 | 8/1994 | von der Decken . |
| 5,368,823 | 11/1994 | McGraw et al. . |
| 5,437,979 | 8/1995 | Rampal . |
| 5,472,672 | 12/1995 | Brennan . |
| 5,474,796 | 12/1995 | Brennan . |
| 5,507,744 | 4/1996 | Tay et al. . |
| 5,529,756 | 6/1996 | Brennan . |
| 5,541,314 | 7/1996 | McGraw et al. . |
| 5,567,122 | 10/1996 | Schulte ..................... 417/214 |
| 5,611,784 | 3/1997 | Barresi et al. . |
| 5,653,259 | 8/1997 | Ramstad . |
| 5,662,671 | 9/1997 | Barbut et al. . |
| 5,700,959 | 12/1997 | Homberg . |
| 5,705,610 | 1/1998 | Zuckermann et al. . |
| 5,730,938 | 3/1998 | Carbonari et al. . |
| 5,736,105 | 4/1998 | Astle . |
| 5,766,556 | 6/1998 | DeWitt et al. . |
| 5,770,157 | 6/1998 | Cargill et al. . |
| 5,788,932 | 8/1998 | Proksa et al. ............ 422/133 |
| 5,975,127 | 11/1999 | Dray ........................ 137/495 |

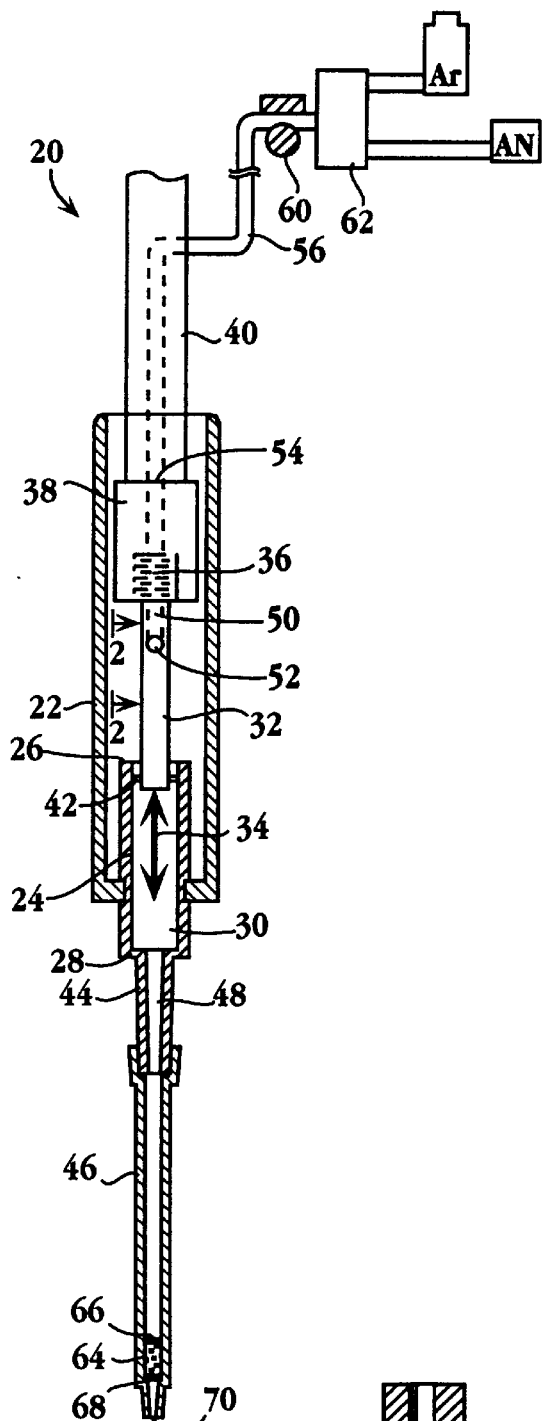
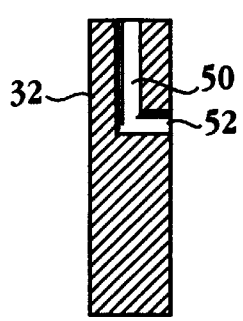
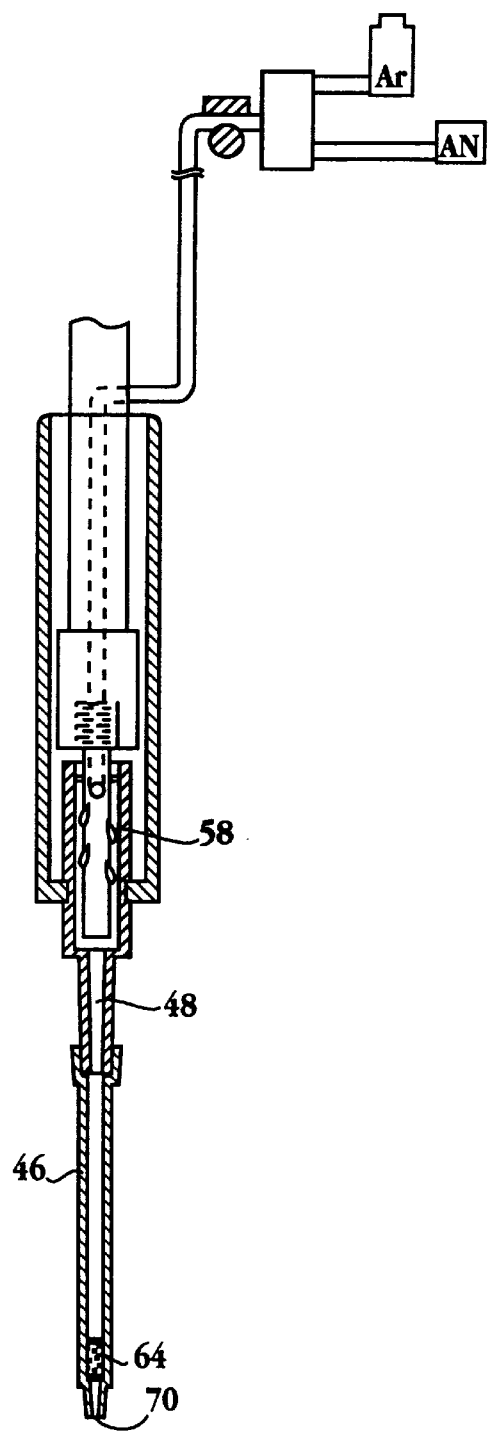
Fig. 1
Fig. 2
Fig. 3

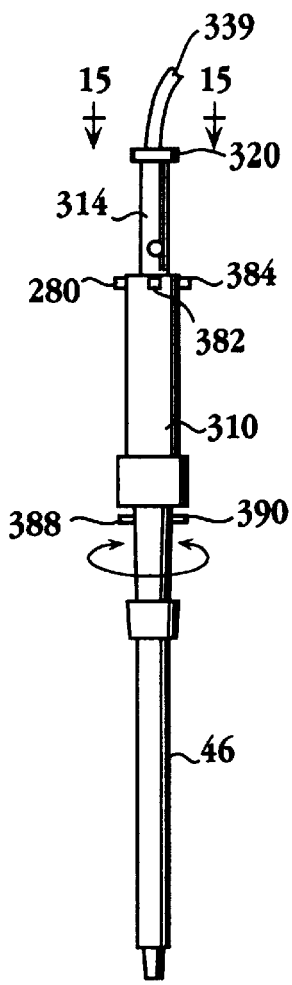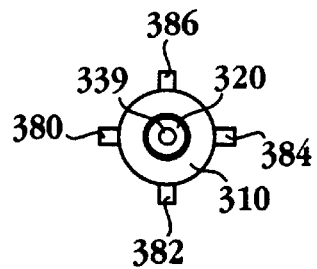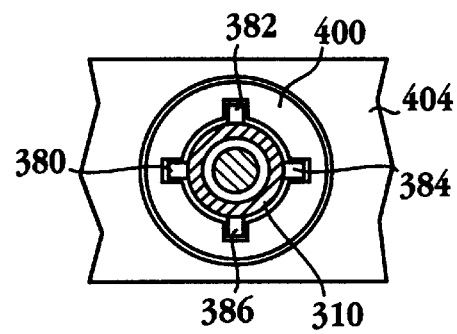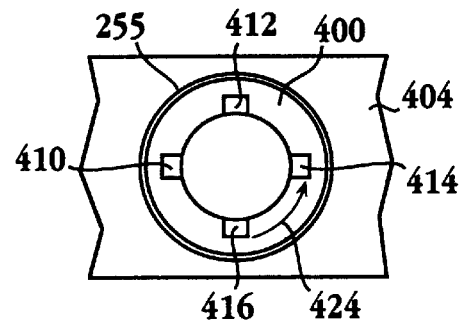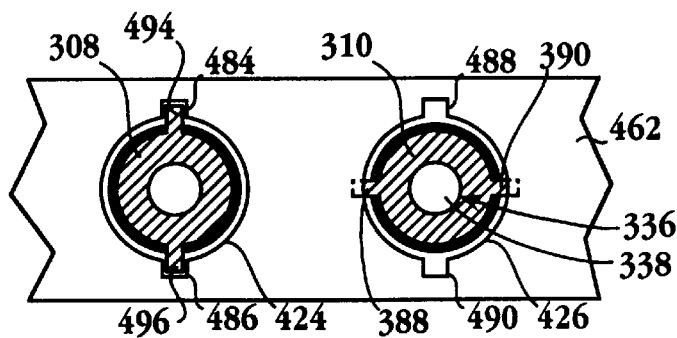
Fig. 19
Fig. 20
Fig. 21
Fig. 22
Fig. 23

PIPETTING DEVICE WITH PIPETTE TIP FOR SOLID PHASE REACTIONS

FIELD OF THE INVENTION

This invention relates, generally, to oligomer synthesis apparatus and methods, and, more particularly, relates to apparatus and methods for multiple and parallel synthesis of different oligonucleotides.

BACKGROUND OF THE INVENTION

With the current growing interest in genome sequencing and mapping, and in PCR applications such as gene probe assays, there is an accelerating demand for oligonucleotide primers. A wide variety of instruments have been developed to meet this demand. A thorough discussion of prior art improvements to the development of methods and apparatus for the chemical synthesis of biopolymers, including polypeptides and oligonucleotides, has been recently provided by Beattie in U.S. Pat. No. 5,175,209 (1992).

In U.S. Pat. No. 5,368,823 (1994), McGraw provides embodiments of an apparatus and method for the automated synthesis of DNA segments utilizing multiple reaction columns, all of which are open at the inlet end to the atmosphere of a reaction chamber. However, the apparatus uses only a single reagent outlet to add reagent to an array of specialized reaction columns. The system is not capable of adding reagent simultaneously to each column, and utilizes costly reaction columns within a complex apparatus.

As another example, Schreuer et aL., (Poster 56, *Fifth International Symposium on Solid Phase Synthesis and Combinatorial Chemical Libraries*, London, England, U.K. Sep. 2–6 1997) describe an array of pipette tips, each retaining a solid support for oligonucleotide synthesis. The tips are held within a reactor module comprising a holder plate that forms the cover of a waste collecting chamber so that the outlet end of each tip is connected to the waste collecting chamber. Liquids applied from above are held within each tip by surface tension and are removed by a vacuum pulse. The module also employs a specialized perforated plate covering the tips to facilitate flow of an inert atmosphere over the open top ends of the tips. In addition, the tips must be manually mounted and removed from the holder plate. Thus the system utilizes a specialized module and is not easily automated.

Sindelar et al., (*Nucleic Acids Res.* 23:982 (1995)) describe a system for high-throughput parallel DNA synthesis. However, their apparatus requires a non-standard multichannel reaction chamber module held within a specialized apparatus using a process which is not readily automated.

In U.S. Pat. No. 5,472,672 (1995) Brennan discloses a polymer synthesis apparatus comprising a manifold comprising a complex array of nozzles, micro-shutoff valves, and dispensing tubes, with each nozzle coupled to a reservoir of liquid reagent, and a base assembly having an array of reaction wells. The reliability of the device is compromised by numerous variables which affect the delivery of liquid reagents from nozzles. The apparatus employs a specially fabricated microtiter plate having reaction wells each for retaining a solid support. The outlet end of each well communicates with a catch basin which is coupled to a vacuum pump to purge the reaction wells. The device utilizes a coated sliding gasket, between the reaction wells and nozzles, which is susceptible to wear or rupture. In addition, the apparatus requires carefully controlled pressure regulation between the top ends of the reaction chambers and their outlet ends. The apparatus requires a laborious and possibly imprecise slurry method for depositing solid support matrix into each reaction well; the support is susceptible to being dislodged during use of the apparatus. Thus, the apparatus requires use of nonstandard microtiter plates, and employs a complex manifold and valve system in an apparatus which incorporates a number of potentially unreliable components.

SUMMARY OF THE INVENTION

Accordingly, it is a general object of the present invention to provide a fast, reliable, inexpensive, flexible and mechanically simple apparatus for high-throughput, continuous, and parallel synthesis of biopolymers in general and oligonucleotides in particular. Another object is to provide an apparatus which primarily utilizes readily available "off the shelf" supplies and systems. Yet another object is to provide a system which is highly automated to reduce labor costs. A further object is to provide an apparatus which can efficiently remove by-products at each sequential step in a biopolymer synthesis in order to increase product yield and purity.

In one aspect, the invention provides a pipetting device for solid phase synthesis. The device comprises a cylinder having an upper end and a lower end and defining a cylindrical chamber extending therebetween, and includes a plunger having an upper and a lower end, wherein the plunger (i) is slidably movable within the cylindrical chamber between a retracted and an extended position, (ii) has an outer diameter that is less than the inner diameter of the chamber, and (iii) has a central passageway leading from a portion of the plunger above the chamber to an egress port which traverses a later wall of the plunger within said chamber. The device also has a seal disposed adjacent the upper end of the cylinder for holding the plunger as it moves. The device has a pipette terminus adapted for mounting a disposable pipette tip. The plunger is movable between (i) a retracted position wherein the egress port is positioned above the chamber, for dispensing liquid when a pipette tip is attached to the pipetting terminus, and (ii) an inserted position wherein the egress port is positioned within the chamber, for introducing a fluid through the passageway into the cylindrical chamber for delivery to a pipette tip when a pipette tip is mounted on the pipetting terminus.

In another aspect, the pipette device can include a pipette tip mounted on the pipetting terminus, and having a solid support for solid phase synthesis in the tip. The solid support can have at least one blocked protected nucleoside, or at least one protected amino acid residue, attached covalently thereto.

In a further aspect, the invention provides an apparatus for solid phase synthesis which comprises a plurality of such pipette devices wherein the plungers of the devices are operatively attached to a plunger plate for simultaneously moving the plungers relative to the cylindrical chambers for liquid dispensing.

In another aspect, the invention provides an apparatus for solid phase synthesis which comprises a plurality of such pipette devices wherein the movement of each device is under separate control of a controller so that each device can be manipulated independently of the other devices in the apparatus. The apparatus can include a power plate for moving the cylinder(s) of one or more of the devices longitudinally, the plate further defining apertures through which the cylinders protrude, and locking means associated with each cylinder for reversibly and separately locking each cylinder to the power plate. The apparatus can further include a plurality of drive motors each having a drive shaft connected to an associated plunger for independent longitudinal movement of each plunger. In one aspect the locking means comprises one or more pin members for locking with the power plate. The power plate includes corresponding recesses for allowing the pin members to traverse the power plate for each cylinder that is in an unlocked position, and the apparatus further includes means for independently rotating each cylinder about its longitudinal axis so that the pin member(s) can be locked to or unlocked from the power plate.

In yet another aspect, the invention involves a solid phase synthesis method comprising the steps of: (a) providing a pipetting device employing a plunger having central passageway as described hereinabove, which further includes a pipette tip mounted on the pipetting terminus, and the pipette tip contains a solid phase synthesis support, (b) drawing a liquid reagent into the pipette tip so that the reagent is contacted for a selected time with the solid phase synthesis support; (c) dispensing the reagent from the pipette tip, and (d) contacting the solid phase synthesis support with a fluid reagent via entry of the fluid reagent through the central passageway into the pipette tip. In the method, the solid support can contain at least one blocked protected nucleotide, or at least one protected amino acid residue, attached covalently thereto. The method is preferably performed simultaneously with a plurality of such devices. The apparatus can include a power plate for moving the cylinder(s) of one or more of said devices longitudinally, the plate further defining apertures through which the cylinders protrude, and locking means associated with each cylinder for reversibly and separately locking each cylinder to the power plate, and step (b) includes the steps of (1) locking the cylinder(s) of one or more of the devices to the power plate, and (2) lowering the power plate toward a liquid reagent tray so that the reagent is contacted for a selected time with one or more solid phase synthesis supports. The fluid reagent can comprise a washing agent effective to remove the first liquid reagent. Examples of a fluid reagent include an organic solvent (e.g., acetonitrile) or an inert gas (e.g., argon).

In still another aspect, the invention concerns a method for synthesizing oligonucleotides comprising the steps of providing an apparatus having a plurality of pipette devices, each employing a plunger having a central passageway as described hereinabove, wherein the plungers of the devices are operatively attached to a plunger plate for simultaneously moving the plungers relative to the cylindrical chamber for liquid dispensing, each device having a tip containing a solid support, wherein each support includes at least one blocked protected nucleotide attached covalently thereto. The method further includes the steps of contacting the supports with a deblocking reagent for a time sufficient to deblock the nucleotide, expelling the deblocking reagent from the supports, and washing all supports by moving the plungers of the apparatus to said inserted position and passing a wash reagent through the supports via the central passageway. The method can further include performing at least one cycle of the following steps: (a) contacting the supports with a deblocking reagent for a time sufficient to deblock the covalently attached nucleotide, expelling the deblocking reagent from the supports, and washing all supports by moving the plungers of the apparatus to the inserted position, passing a wash reagent through the supports via said passageway, and drying the supports, so that the attached nucleotides are deblocked; (b) contacting the supports with a selected blocked protected nucleotide under conditions effective to append the selected blocked protected nucleotide to the deblocked nucleotide on each support, expelling residual blocked protected nucleotide; (c) contacting the supports with capping reagent to block unreacted residues; (d) contacting the supports with a selected oxidizing reagent to convert any phosphite phosphorus atoms to the +5 formal state, expelling the oxidizing reagent from the support, and washing and drying the supports.

In yet another aspect, the invention involves a tip remover for use with a multi-channel pipetting apparatus. In one embodiment, the tip remover comprises a plurality of elongated chambers arranged in a plane and opening in alignment with said apparatus for receiving each tip when said apparatus is moved into a position vertically adjacent said tip remover, each chamber having retractable fingers extending therefrom, the fingers adapted for reversibly engaging a selected tip such that only the selected tip is retained by the tip remover when the apparatus is moved vertically away from said tip remover.

The tip remover can include means (e.g., a solenoid) for moving the fingers longitudinally within each chamber. The fingers can comprise a pair of elongated fingers extending longitudinally within each chamber. The fingers can be movable between a retracted position and an extended position within each chamber. In the extended position, the fingers spread for receiving a tip, and wherein in the retracted position the fingers engage a portion of the selected tip. The selected tip can have an annular rim or flange. In the retracted position, the fingers engage the annular rim or flange.

BRIEF DESCRIPTION OF THE DRAWINGS

FIG. 1 is a cross-sectional view of a single pipette device of the invention showing the plunger in a retracted position;

FIG. 2 is a cross-sectional side view of the plunger of the device of FIG. 1 taken along the lines 2—2;

FIG. 3 is a view of the single pipette device of FIG. 1 showing the plunger in an inserted position;

FIG. 19 is a side view of a pipette employed in the apparatus of FIG. 16;

FIG. 20 is a top view of the pipette of FIG. 19;

FIG. 21 is a partially cross sectional view of the support plate taken along the sectional lines labeled 21—21 in FIG. 18;

FIG. 22 is a view of the support plate taken along the sectional lines labeled 22—22 in FIG. 18;

FIG. 23 is a view of the power plate taken along the sectional lines labeled 23—23 in FIG. 17;

DETAILED DESCRIPTION OF THE INVENTION

Figures 4, 5:
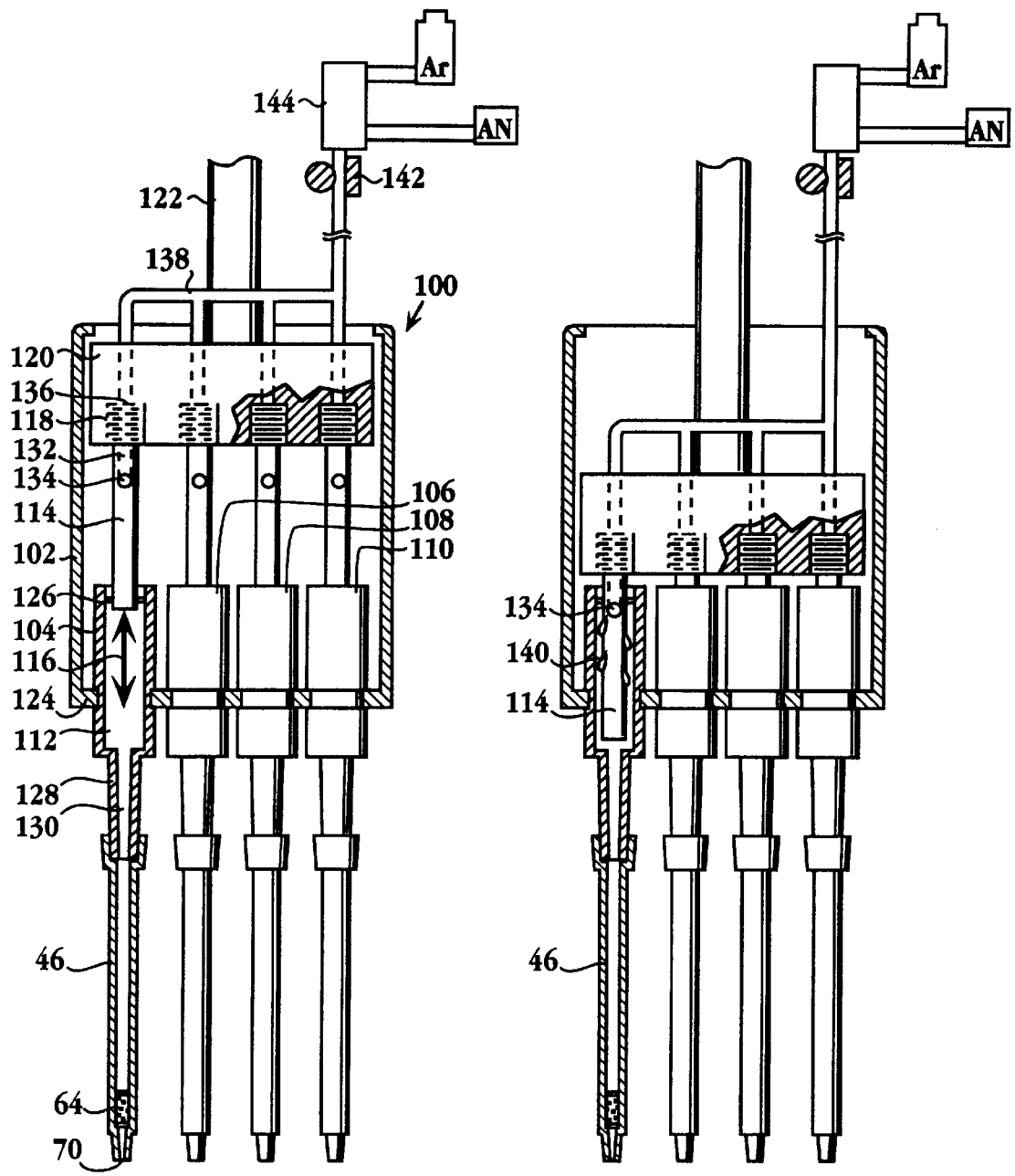
FIG. 4 is a partially cross-sectional view of a first embodiment of a multi-channel apparatus of the invention with the plungers in a retracted position.
FIG. 5 is a cross-sectional view of the apparatus of FIG. 4 with the plungers in an inserted position.

Referring now to the Drawings, provided for illustrative purposes only and not intended as a limitation on the invention disclosed herein, similar or identical elements are give consistent identifying numerals throughout the various figures thereof and parenthetical references to figure numbers direct the reader to the view(s) in which the element(s) being described is (are) best or alternatively seen, although the elements(s) may be seen also in other views.

Referring primarily now to FIGS. 1–3, there is illustrated a reaction device 20 according to one embodiment of the present invention. The preferred device is adapted to be used with an automated apparatus such as a computer-controlled bench-top system (not shown) designed for the performance of pipetting operations (e.g., the systems described in U.S. Pat. No. 5,306,510, and International Publication No. WO 97/26539). The device includes a housing 22 containing a cylinder 24 having an upper end 26 and a lower end 28 which define a cylindrical chamber 30. A plunger 32 is disposed within the cylinder for movement therein as indicated by double-headed arrow 34 to provide for the aspiration or expulsion of fluids from said cylinder. The volume aspirated or expelled will be understood is determined by the diameter of the plunger as well as the length of stroke thereof. The head 36 of the plunger is within block 38 which is connected to rod member 40 which is operably connected to an actuating means, such as a motorized helical screw (not shown), for raising and lowering the plunger. The plunger 32 is sealed to the inner walls of cylinder 24 by means of a suitable seal, as for example O-ring 42. O-Ring 42 is unreactive with reagents such as organic solvents or other solutions with which it comes in contact in the operation of the invention as described herein. The O-ring is preferably made of Buna-N rubber (Spec Seals, Anaheim, Calif.) or KALREZ (DuPont Dow Elastomers, Wilmington, Del.) and is retained, for example, within a recessed channel (not shown). At the lower end of the cylinder is an attachment fitting, such as a tip holder 44, which is configured for detachably holding a fluid receptacle, such as a pipette tip 46, which defines a passage 48 in tip holder 44 is in fluid communication with chamber 30.

Plunger 32 contains a central passage 50 which extends through the upper portion of plunger 32 and communicates with an egress port 52 which traverses a wall of said plunger and also with opening 54 in an upper end of the plunger. Opening 54 is connected to a conduit such as tubing 56 for delivery of fluids to chamber 30 as described hereinbelow. The plunger is movable between a retracted position (FIG. 1), for aspirating and dispensing of liquids (as indicated by double headed arrow 34), and an inserted position (FIG. 3). While in the retracted position, port 52 remains above O-ring 42. In the inserted position, the port 52 is below O-ring 42, and fluid 58 can be introduced into the chamber 30 from tubing 56. In a preferred embodiment, tubing 56 is regulated, e.g., by pinch valve 60, and is connected to valve means 62 for selectively switching between a source of inert gas (e.g., argon) and a source of washing fluid (e.g., acetonitrile). A particular advantage of central passage 50 and egress port 52 is that they provide a simple means for the application of fluids to the top of the solid matrix without requiring additional valves for regulating the application of such fluids during the use of the device 20 for aspiration and expulsion of liquids.

A plurality of reaction devices can be configured in an array, such as a 1 by 8, 8 by 12, or other array, to be used with standard microtiter plates. In a preferred embodiment, the apparatus consists of a multi-channel apparatus, as illustrated in FIGS. 4 and 5 (a 1 by 4 array apparatus is shown for ease of illustration).

In operation, the single- or multi-channel apparatus can be used in conjunction with pipette tips containing a reaction chamber. The preferred tips contain a solid support 64 within the reaction chamber for performing chemical reactions within the chamber. The tip is modified or adapted to hold the solid support in a secure manner while still permitting the free flow of fluids into and out of the pipette tip. This can be achieved, for example, by securing porous frits 66,68 of an inert material such as glass or plastic, secured inside the pipette tip 46 by a friction fit.

The solid phase support may be any insoluble macroscopic solid material on which the first reactant or chemical species involved in the reaction sequence can be immobilized. The method of immobilization may be any method by which the species is securely fixed to the support and yet capable of release upon completion of the reaction sequence. Preferred methods of immobilization are covalent bonds, and preferred solid supports are accordingly those which have surface functional groups readily susceptible to the formation of covalent bonds with the chemical species, or those which are readily activated or derivatized by the attachment of such functional groups. With these considerations in mind, any of the wide range of conventional materials used in the biotechnology art as solid supports may be used. Examples are silica glass, controlled port glass (CPG), polystyrene, cellulose, and Sepharose (agarose). A preferred support for oligonucleotide synthesis is highly crosslinked porous polystyrene as described in U.S. Pat. No. 5,047,524. Supports suitable for solid phase peptide synthesis are described in U.S. Pat. No. 5,026,773. The form of the solid phase support may also vary. Any form which will provide ample surface area accessible to liquids flowing through and permit the flow of the liquids to achieve full contact may be used. Examples of usable forms are gels, particles or beads.

The apparatus of the present invention can be used in any repetitive chemical process requiring synthesis or degradation which can be done on a solid phase. For example the apparatus can be used in the synthesis of a variety of oligomers such as polypeptides, polysaccharides, and oligonucleotides. The discussion to follow will reference oligonucleotide synthesis for the sake of simplicity only and not by way of limitation.

The term "oligonucleotide" refers to polymers of nucleotide monomers or nucleic acid analogs thereof, including double and single stranded deoxyribonucleotides, ribonucleotides, (-anomeric forms thereof, and the like. Usually the monomers are linked by phosphodiester linkages, where the term "phosphodiester linkage" refers to phosphodiester bonds or bonds including phosphate analogs thereof, including associated counterions, e.g., $H^+$, $NH_4^+$, and $Na^+$. Oligonucleotides typically range in size from a few monomeric units, e.g. 5–40, to several thousands of monomeric units. Whenever an oligonucleotide is represented by a sequence of letters, such as "ATGCCTG," it will be understood that the nucleotides are in 5' to 3' order from left to right and that "A" denotes deoxyadenosine, "C" denotes deoxycytidine, "G" denotes deoxyguanosine, and "T" denotes deoxythymidine, unless otherwise noted. "Nucleoside" refers to a compound consisting of a purine, deazapurine, or pyrimidine nucleobase, e.g., adenine, guanine, cytosine, uracil, thymine, deazaadenine, deazaguanosine, and the like, linked to a pentose at the 1'-position. When the nucleoside base is purine or 7-deazapurine, the pentose is attached to the nucleobase at the 9-position of the purine or deazapurine, and when the nucleobase is pyrimidine, the pentose is attached to the nucleobase at the 1-position of the pyrimidine.

"Nucleotide" refers to a phosphate ester of a nucleoside, e.g., a triphosphate ester, wherein the most common site of esterification is the hydroxyl group attached to the C-5 position of the pentose. A nucleotide is composed of three moieties: a sugar, a phosphate, and a nucleobase (Blackburn, G. and Gait, M. Eds. *DNA and RNA structure" in Nucleic Acids in Chemistry and Biology*" 2nd Edition, (1996) Oxford University Press, pp. 15–81). When part of a duplex, nucleotides are also referred to as "bases" or "base pairs".

The term "nucleic acid analogs" refers to analogs of nucleic acids made from monomeric nucleotide analog units, and possessing some of the qualities and properties associated with nucleic acids. Nucleic acid analogs may have modified (i) nucleobase moieties, e.g. C-5-propyne pyrimidine, pseudo-isocytidine and isoguanosine, (ii) sugar moieties, e.g. 2'-O-alkyl ribonucleotides, and/or (iii) internucleotide moieties, e.g. 3'-N-phosphoramidate (Englisch, U. and Gauss, D. Angew. *Chem. Int. Ed. Engl.* 30:613–29 (1991)). A class of analogs where the sugar and internucleotide moieties have been replaced with an 2-aminoethylglycine amide backbone polymer is peptide nucleic acids (Nielsen, P., Egholm, M., Berg, R. and Buchardt, O. *Science* 254:1497–1500 (1991)).

The apparatus of the invention can be used to carry out conventional chemical oligonucleotide synthesis which includes the following steps: deblocking (detritylation), condensation with phosphoramidite, capping, and oxidation (e.g., as described in U.S. Pat. No. 5,047,524). These steps are repeated until the desired sequence is obtained. The product is released from the solid matrix by liquid or gaseous ammonium treatment (e.g., as described in International Publication No. WO 97/26540 and U.S. Pat. No. 5,047,524). In a preferred method, a wash treatment with a washing agent follows each reaction in order to remove residual reagents such as deblocking agent, phosphoramidite, oxidizer, or residual water which can cause by-product formation and reduced yields of the desired product. Examples of washing agents include organic solvents such as hexane, acetonitrile and methylene chloride. A preferred washing agent is acetonitrile.

Also in a preferred method, the solid phase matrix is dried by exposure to an inert gas, such as argon, as admitted through the same egress port 52 after each washing treatment for removing residual washing agent and for preparing the solid matrix for the subsequent reaction step.

When prior art pipette devices are used with the modified tips described hereinabove, only an up-and-down movement of liquid within a tip is possible. Thus, in a wash treatment step, only a "bidirectional" wash can be achieved since the washing 10 agent can only be aspirated and then expelled from the bottom end 70 of the tip.

Furthermore, there is no means for readily applying an inert gas for drying the solid matrix.

The present invention is based in part on Applicants' unexpected discovery that "unidirectional" application (i.e., from the top of the tip and toward the bottom) of washing and drying agents, as made possible using the present invention, gave superior product purity and yield compared to using bi-directional application of these agents. When a synthesis of oligonucleotide was performed using a prior art pipette device, low product yields were obtained, even with multiple bidirectional washing treatments with acetonitrile after each reaction step. For example, when a conventional pipette was used, with bidirectional washing steps, in the synthesis (as further described hereinbelow) of a single stranded oligonucleotide containing six thymidines (T6), the product purity was about 62%, whereas the use of a device of the present invention, using unidirectional washing steps, gave a yield of over 95% with approximately 30% higher product yield. The invention overcomes the inability of prior art pipettes to apply fluid unidirectionally to the top of an attached tip. Unlike prior art pipette devices, the present device makes possible efficient washing and drying of the solid phase support after any selected step of the synthetic process. Although the invention will be described hereinbelow in reference to its utility in applying washing and drying agents, the invention also provides a means for the application of any desired gaseous or liquid reagent to the top of the solid support.

In the operation of the instant invention, when it is necessary to wash the solid support, the pipette plunger 32 is moved to an inserted position (FIG. 3). Valve 60 is opened and fluid (e.g., acetonitrile) traversing passage 48 enters the top of the pipette tip, continues downstream to wash the solid support 64 retained within the tip, and thence emerges through opening 70. Similarly, an inert gas can be introduced for drying the solid support using valve 62.

In another embodiment of the present invention, a syringe device can be used to aspirate and deliver liquid reagent in analogy to the pipette as described hereinabove.

Figure 6:
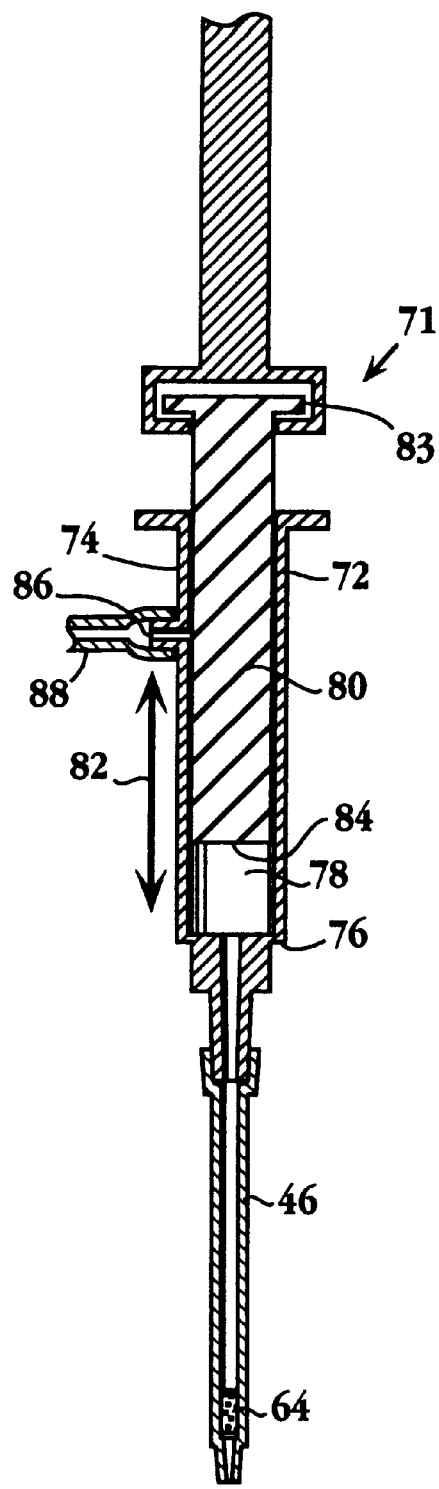
FIG. 6 is a cross-sectional view of a syringe device in an inserted position.
Figure 7:
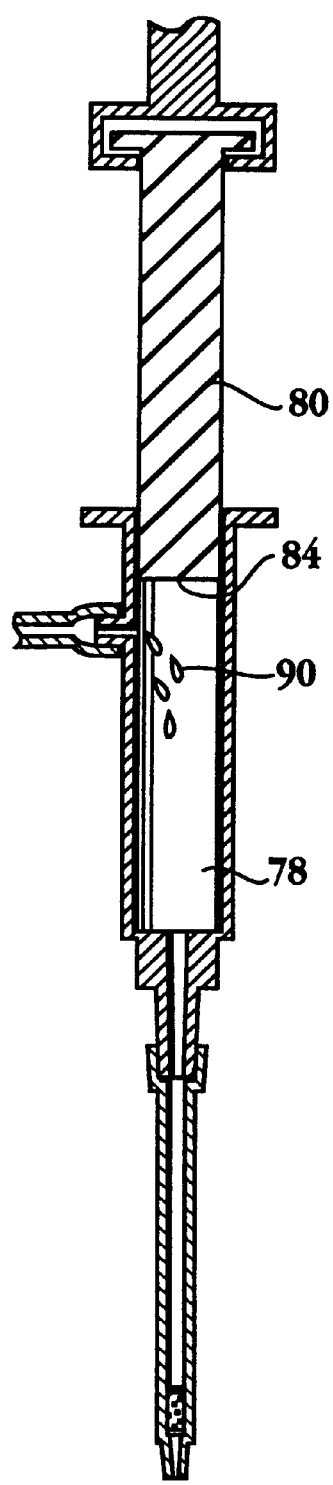
FIG. 7 is a cross-sectional view of the syringe device of FIG. 6 in a retracted position.

FIG. 6 illustrates an example of such a syringe 71 which includes a cylinder 72 having an upper end 74 and a lower end 76 which define a cylindrical chamber 78. A plunger 80 is disposed within the cylinder for movement therein such as indicated by the double-headed arrow 82. The head 83 of the plunger 80 can be actuated by conventional means, such as a helical screw (not shown), for raising and lowering the plunger. The plunger optionally has a seal (not shown) at its lower end 84 in contact with the walls of the cylinder. In the embodiment shown, the cylinder is provided with a port 86. The plunger is movable between an inserted position FIG. 6 for aspirating and dispensing of liquids, and a retracted position FIG. 7. While in the inserted position, port 86 remains above the lower end of the plunger. In the retracted position, port 86 is below the lower end 84 of the plunger so that fluid 90 can be introduced into the chamber 78 such as from tubing 88. In analogy with the pipette device described hereinabove, when used with a modified pipette tip 46, the syringe can be used in the inserted position for dispensing and aspirating fluids for contacting a solid support 64 retained in the tip, and can be used in the retracted position for washing a solid support retained in the tip.

In another aspect the present invention comprises an array of pipettes (or syringes) which can be used for carrying out parallel synthesis of oligonucleotides on solid supports. In one embodiment of a multi-channel pipette apparatus, all of the pipette plungers move in unison, i.e., their movement is common and coordinated. A robotic system (e.g., Biomek 2000, Beckman Coulter, Inc., Fullerton, Calif.) equipped with such an apparatus allows the parallel aspiration and delivery of liquid samples. Suitable robotic systems are also available from Tecan (Research Triangle Park, N.C.), Hamilton (Reno, Nev.), and TomTec Instruments (Hamden, Conn.). The liquid reagents can be contained in an array of vessels or reservoirs, such as the wells of microtiter plates, or in a single vessel such as a trough. The spacing and arrangement of the multi-channel pipette apparatus of the present invention preferably is complementary to spacing found in existing fluid handling systems, e.g., compatible with mutiwell plate dimension. For example, in preferred aspect, the pipettes (or syringes) are positioned or arranged in a linear format (e.g., along a line) or gridded fashion at regularly spaced intervals. For example, in preferred embodiments, the pipettes of the apparatus are arranged on approximately 9 mm centers (96-well plate compatible) in a linear or gridded arrangement, more preferably, 4.5 mm centers (384 well plate compatible) and most preferably, on approximately 2.25 mm centers (1536 well plate compatible).

For clarity of presentation, and not by way of limitation, pipette devices will be described hereinbelow, it being understood that analogous syringe devices can also be employed. Referring primarily now to FIGS. 4 and 5, there is illustrated a multi-channel apparatus 100 according to one embodiment of the present invention. The preferred apparatus is adapted to be used with an automated system such as a computer-controlled bench-top system designed for the performance of pipetting operations. The apparatus as shown in FIG. 4 is mounted within housing 102 and includes cylinders 104, 106, 108, and 110 (analogous to device 20), each having an upper end and a lower end which each define a cylindrical chamber such as shown at 112. As exemplified by cylinder 104, a plunger 114 is disposed within each cylinder for movement therein as indicated by double-headed arrow 116. The head of plunger 118 is retained within plunger plate 120 which engages rod 122 connected to actuating means (not shown), such as a motorized helical screw, for raising and lowering the plunger. The cylinders are held in parallel by a bottom portion 124 of said housing. Each plunger is sealed to the inner walls of the associated cylinder (e.g., at 104) by means of a suitable seal, as for example elastomeric O-ring 126. O-Ring 126 is composed preferably of a material unreactive with liquid reagents, such as organic solvents, which will be introduced into chamber 112 in the operation of the invention. At the lower end of the cylinder is a fitting, such as a tip holder 128, which is configured for detachably holding a fluid receptacle, such as a pipette tip 46. A passage 130 in tip holder 128 is in fluid communication with chamber 112. Each plunger contains a central passage, in analogy with device 20. For example, plunger 114 contains a passage 132 which extends through the upper portion of the plunger and communicates with egress port 134 and also with opening 136 in an upper portion of the plunger. Opening 136 is connected to a conduit, such as tubing 138, for delivery of fluids to chamber 112 and to the chambers of the other cylinders. The plunger is movable between a retracted position (FIG. 4), for aspirating and dispensing of liquids (as indicated by double-headed arrow 116), and an inserted position (FIG. 5). While in the retracted position, port 134 remains above seal 126. In the inserted position, port 134 is below seal 126 (FIG. 5), and fluid 140 can be introduced from tubing 138 into each cylinder chamber. In a preferred embodiment, tubing 138 is regulated, e.g., by valve 142, and is connected to valve means 144 for selectively switching between a source of gas and a source of washing fluid.

During the synthesis of oligonucleotides using a pipette or syringe as described hereinabove, the solid support contained within the tip is exposed to a succession of different chemical reagents by the aspiration and expulsion of the reagent through the end 70 of the tip 46.

In one aspect of the invention, synthesis of oligonucleotides is carried out using a plurality of pipettes or syringes arranged in an array, with the solid support in each tip exposed to a succession of chemical reagents in parallel. In the embodiment of the apparatus shown in FIGS. 4 and 5, the plungers move in unison to aspirate or expel chemical reagent. The cycle of steps for the addition of each nucleotide includes a condensation step in which it is necessary to expose each solid support to only a selected phosphoramidite which is to be incorporated at a desired position in the oligonucleotide sequence. For example, when using a 96-well microtitre plate, each well contains a selected phosphoramidite. Such a plate is referred herein as a "non-uniformly filled plate" since, typically, not all of the wells will contain the same reagent.

By contrast, the use of a "uniformly filled plate," in which all of the wells contain the same reagent, will be described hereinbelow in another aspect of the invention.

Figure 8:
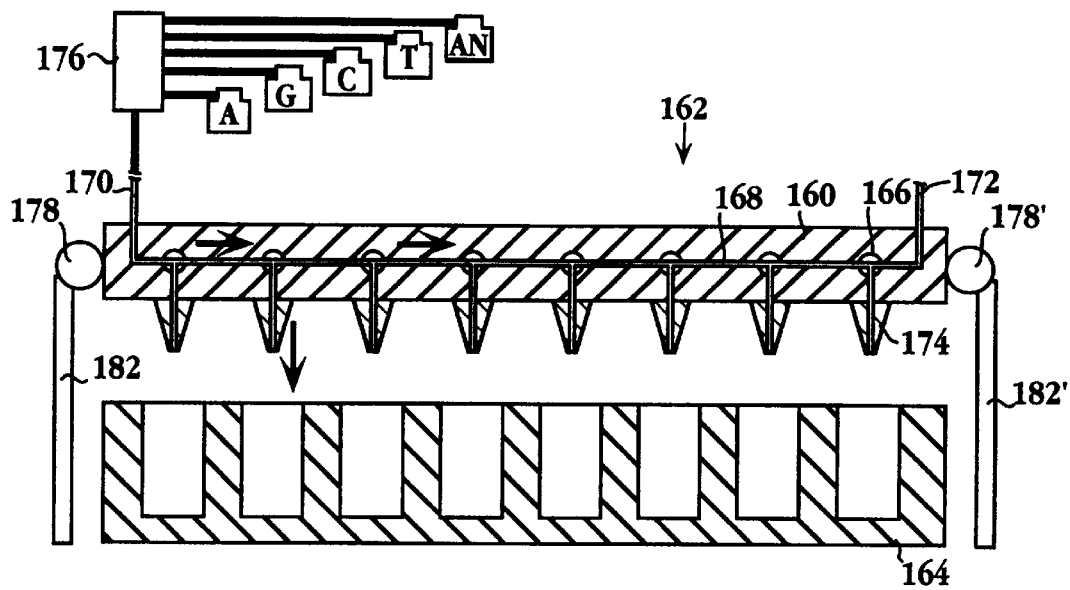
FIG. 8 is a cross-sectional frontal view of an overhead fill rack apparatus.
Figure 9:
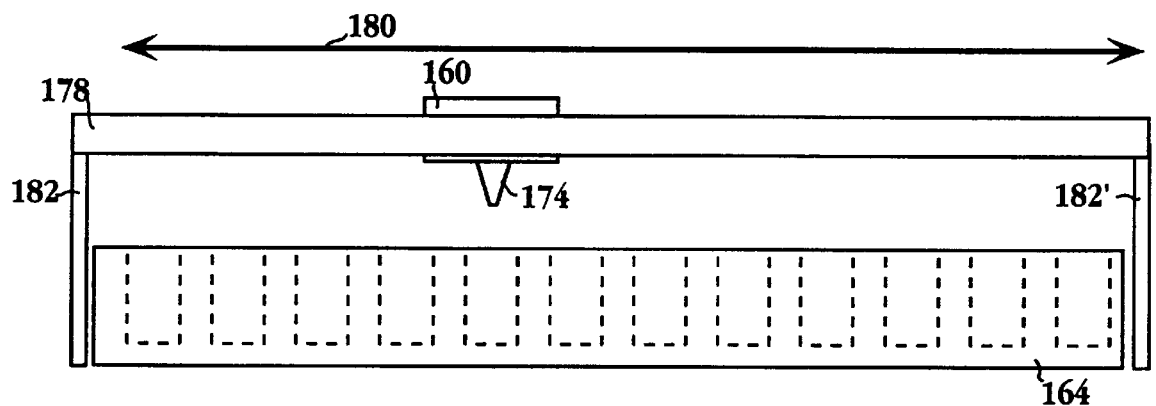
FIG. 9 is a side view of the apparatus of FIG. 8.

A non-uniformly filled plate can be prepared using a robotic system utilizing a conventional single-channel pipette device to transfer selected reagent successively to each well. Preferably, however, the transfer to the wells is performed simultaneously. The ability to add phosphoramidite reagents selectively and simultaneously to multiple wells to form a non-uniformly filled plate is an important aspect of the invention. Applicants have designed reagent delivery systems in order to accomplish the parallel transfer of reagents to multiple wells of a multi-well plate. In one embodiment of this aspect of the invention, a valved filler block 160 is positioned in an overhead fill rack apparatus 162 above a multi-well plate 164 (FIGS. 8 and 9). Block 160 includes valves, such as 3-way valves 166, connected to a common reagent line 168, inflow conduit 170, and outflow conduit 172, and delivery nozzles, such as at 174, aligned with wells as described herein. The inflow conduit 170 is connected to a manifold 176 which receives reagent from pressurized bottles. In one embodiment, block 160 and manifold 176 each comprise a valve block as described in U.S. Pat. No. 5,653,259. The filler block 160 illustrated is an 8 by 1 array, although other arrays could be used. In operation, the filler block 160 is movable along guide rails 178,178' (in the general direction shown by arrow 180) which are supported by vertical support members 182, 182'. The block moves from one end of a multi-well plate to another and pauses at each row of 8 wells for delivering liquid reagent therein. At each row, selected valves are set either to a delivery position for delivering reagent to the wells or a bypass position (not shown). Filler block 160 and manifold 176 are under control of a computerized controller (not shown). A first reagent, such as one of the phosphoramidites, is introduced into the inflow conduit 170 and distributed to the selected delivery nozzles which are set in the delivery position. The valves are then all set to the bypass position and the common reagent line 168 is flushed with solvent which empties into outflow conduit 172. Before the block moves to the next row the valves are similarly repositioned (e.g., up to three more times such as when adding the four phosphoramidites) to deliver other reagents to selected wells in the row. The 96-well plate 164 remains stationary throughout the filling process.

After the plate is filled, the block 160 is moved aside. Alternatively, the completed multi-well plate can be moved to a position away from the apparatus 162. A 96-channel pipette apparatus, as described in the present invention, equipped with tips containing support matrix is moved into position above the multi-well plate and simultaneously aspirates reagent phosphoramidites from the non-uniformly filled plate. The 96-channel apparatus then proceeds to other reagent stations as described hereinbelow. The 96-well plate can be removed and replaced with a fresh plate. Alternatively, a refillable plate (such as available from Polyfiltronics, Inc., Rockland, Mass.) having frits and outflow channels at the bottom of each well can be used, with vacuum suction of unused reagent, followed by a solvent rinse after the aspiration step (not shown).

Figure 10:
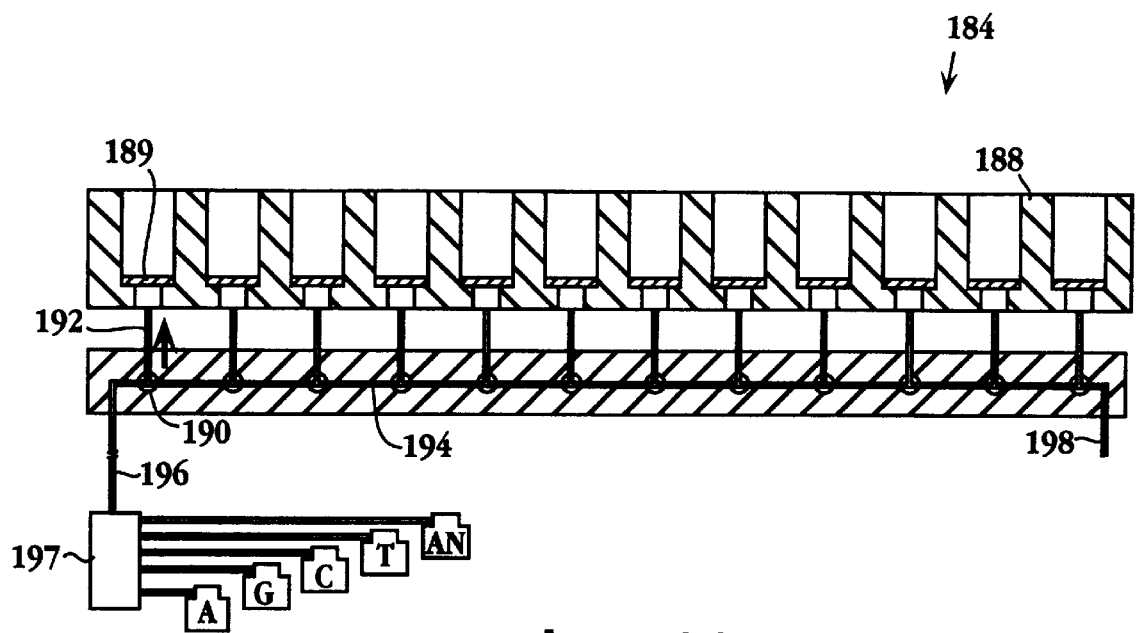
FIG. 10 is a cross-sectional frontal view of an underneath fill apparatus.
Figure 11:
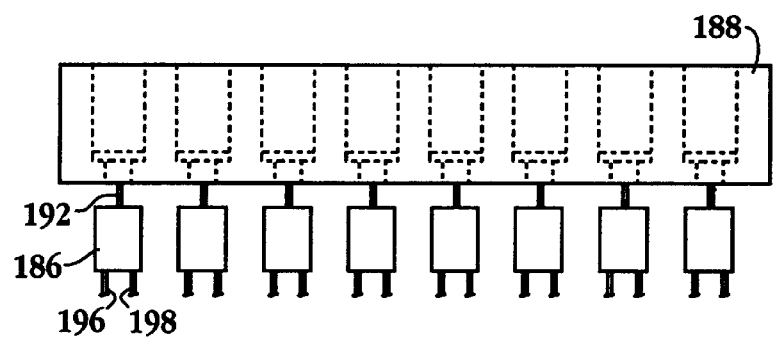
FIG. 11 is a schematic side view of the apparatus of FIG. 10.

Another embodiment of this aspect of the invention is an underneath fill apparatus 184 which includes a plurality of parallel multi-valved filler blocks such as at 186 positioned underneath the rows of a refillable multi-well plate 188 (FIGS. 10 and 11) which includes frits, such as at 189 in the bottom of each well. In the illustration, each filler block 186 has eight valves (such as shown at 190), fill conduit 192 in fluid communication with the bottom of each well, a common reagent line 194, an inflow conduit 196, and an out flow conduit 198. In use, the valves in each filler block are set to either a delivery position or a bypass position (not shown). In analogy with block 160, as described hereinabove, reagent enters the common reagent line from inflow conduit 196 and is delivered only to those wells connected to valves which are set in the delivery position. Between reagent additions, the valves can all be set to the bypass position, and the common reagent line 194 can be flushed with solvent which empties into outflow conduit 198. Filler block 186 and manifold 197 are under control of a computerized controller (not shown). In one embodiment, block 186 and manifold 197 each comprise a valve block as described in U.S. Pat. No. 5,653,259.

It will be appreciated that an apparatus such as 162 or 184 can also be used to deliver other chemical reagents, as described herein, required in oligonucleotide synthesis.

During the parallel synthesis of oligonucleotides, certain oligonucleotides in the array will be completed before others. In one embodiment of a method of synthesis, in order to avoid exposing the completed oligonucleotides to further deblocking, oxidizing, or capping agents, which can damage completed oligonucleotides, it is preferable that all of these reactive agents, in addition to the phosphoramidites, are utilized in a non-uniformly filled plate format. For example, for those tips containing a completed oligonucleotide sequence, the corresponding well in any subsequent multi-well plates will not contain any reactive agent (i.e., will not be filled). However, during the synthetic steps required of the longer oligonucleotides, the corresponding wells for these longer oligonucleotides will continue to be filled with reactive agent as needed. In a preferred method of synthesis, as will be described below, tips having completed oligonucleotides are selectively removed from the multi-channel apparatus as soon as they are completed.

Figure 14:
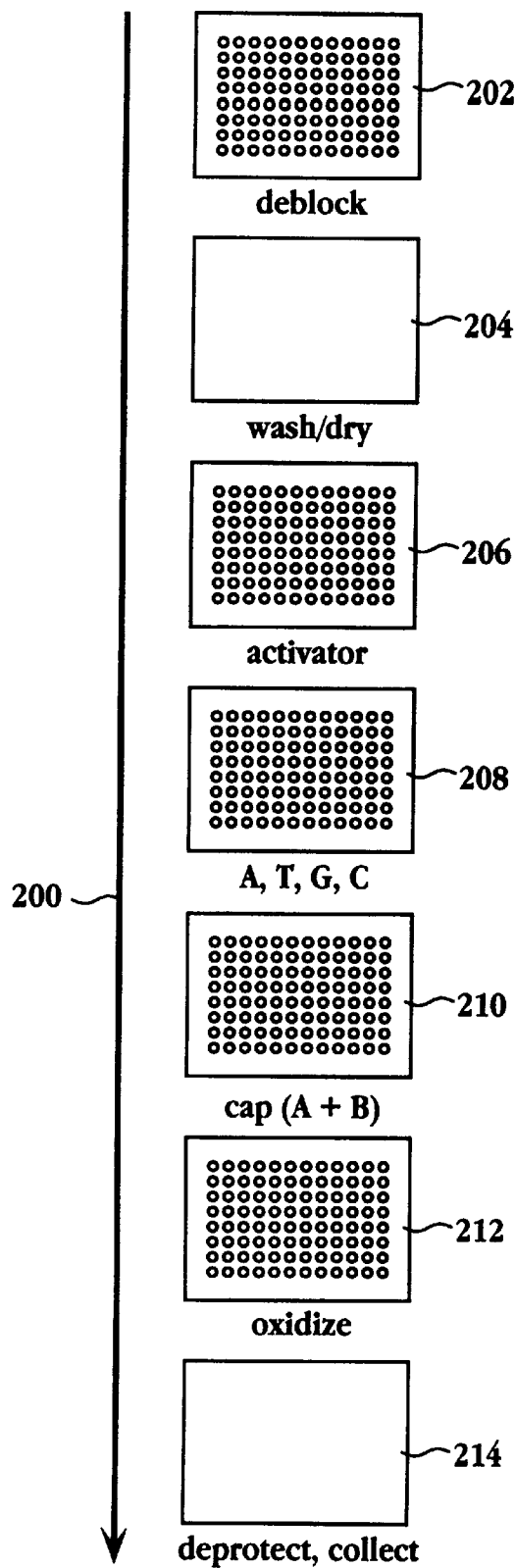
FIG. 14 is a schematic diagram of a first layout of a series of reagent stations for use in oligonucleotide synthesis.

FIG. 14 schematically illustrates an arrangement of troughs (represented by rectangles) and non-uniformly filled multi-well plates containing reagents for oligonucleotide synthesis by a computer controlled bench-top system equipped with an overhead multi-channel pipette apparatus capable of simultaneous aspiration and delivery of liquids (e.g., as illustrated at 100). A preferred apparatus has 96 pipettes arranged for alignment with a 96-well plate disposed beneath the apparatus.

With the description of an embodiment of the apparatus now complete, a description of a particular process using the inventive apparatus follows. Prior to the operation of the instrument, the various oligonucleotide sequences to be produced by the device are entered into a text file and located on either a diskette or other memory device of a computer. A program to control the operation of the multi-channel apparatus and the transport of the apparatus between station is located within RAM. The control program accesses the desired text file and directs the automated synthesis of DNA according to the sequences found therein.

Figure 12:
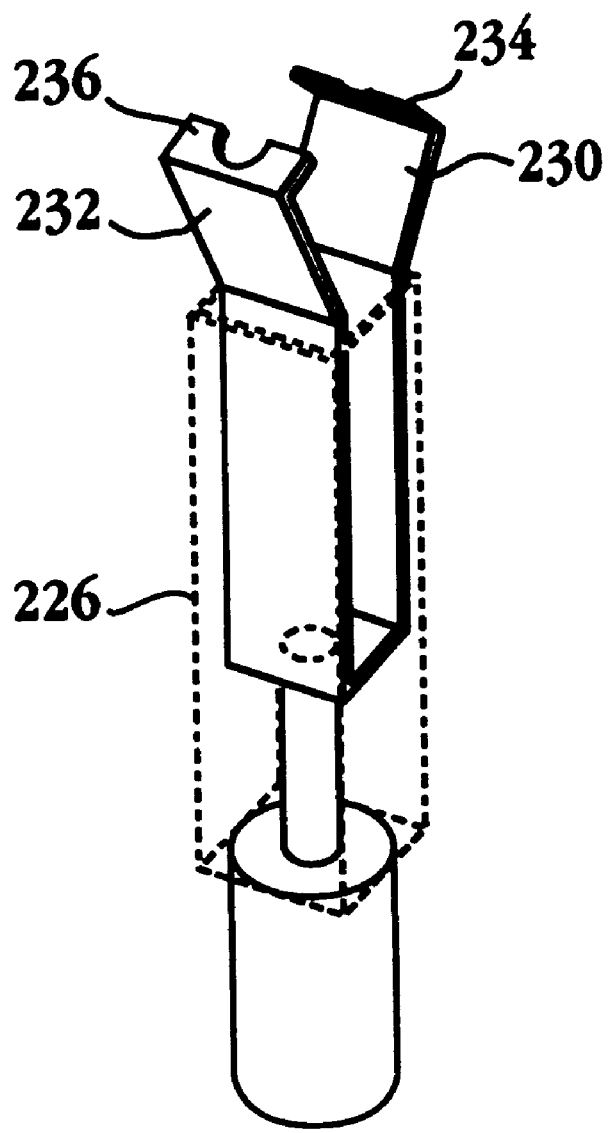
FIG. 12 is a perspective view of an embodiment of a tip puller.

Prior to the beginning of the operation, the tips to be attached to the apparatus are prepared with appropriate solid support. The supports can contain different nucleoside materials (e.g., different blocked nucleosides) one from another so that different sequences can be produced concurrently in the inventive apparatus. When the synthesis program is started, the instrument enters the first synthetic cycle. A synthetic cycle consists of the following reactions:

In the operation of this aspect of the invention, for each base to be added to a growing chain, the pipette apparatus proceeds through different stations generally along the direction indicated by arrow 200 (FIG. 14). A synthetic cycle for the addition of each nucleotide begins at station 202. Station 202 contains reagent deblocking chemical; station 204 is an area for performing a washing and drying procedure; station 206 contains activator; station 208 comprises a non-uniformly filled plate containing reagent coupling agent (i.e., phosphoramidite(s)); station 210 contains reagent capping chemical; station 212 contains reagent oxidizing chemical. The apparatus returns to station 202 to repeat the cycle if other phosphoramidites are to be added to a growing chain. A fresh non-uniformly filled plate containing selected phosphoramidite(s) to be added can be provided at station 208 during each cycle, or a refillable plate can be used as described in relation to FIGS. 10 and 11. In a preferred method, after each reactive step, the apparatus is positioned at station 204 and the solid support is washed unidirectionally with solvent such as acetonitrile and then dried by inert gas such as argon. For this washing and drying process, plunger plate 120 is lowered by rod 122 so that ports, such as at 134, are below an associated O-ring, in analogy to device 20. A station for deprotection and collection of product is indicated at 214. Tips can be removed (for example as described herein in relation to FIGS. 12 and 13) from the apparatus at this station for those tips containing completed oligonucleotides.

Table 1 presents an example of chemical reagents for use in synthesizing the oligonucleotide sequences.

It should be understood that the particular chemicals shown in Table 1 are illustrative of those chemicals used in a successful operation but the apparatus and methodology of the invention are not limited to any specific coupling chemistry.

TABLE 1

DNA Synthesis Reagents

| Common Name | Composition |
|---|---|
| WASH | Acetonitrile |
| DEBLOCK | 2.5% dichloroacetic acid in methylene chloride |
| ACTIVATOR | 3% tetrazole in acetonitrile |
| A,C,G,T | 2.5% cyanoethyl phosphoramidite in acetonitrile |
| OXIDIZER | 2.5% iodine in 9% water, 0.5% pyridine, 90.5% THF |
| CAP A | 10% acetic anhydride in tetrahydrofuran (THF) |
| CAP B | 10% 1-methylimidazole, 10% pyridine, 80% THF |

Incubation times and the number of reagent additions at each step in the synthetic cycle vary depending on the reagent.

Steps can be repeated if necessary. Values for a successful protocol are given in Table 2 below. Two of the steps require mixing of reagents. That is, the coupling step requires mixing of phosphoramidite and activator and the capping step requires mixing of the Cap A and Cap B solutions. Mixing can be accomplished in-line, for example, when reagents are delivered from an apparatus such as described in FIGS. 8 or 11.

At each station, sufficient volume is aspirated to provide substantially complete coverage of the surface of the solid support retained in the tips.

Due to the unstable nature of some of the reagents involved in oligonucleotide synthesis, especially the phosphoramidites and tetrazole, it is preferable that the plates holding these reagents be prepared just prior to use (i.e., "just-in-time"). It is also preferable to carry out the synthetic reactions under an inert atmosphere, e.g., in a glove box, and in the presence of drying agent (e.g., DRIERITE).

TABLE 2

Incubation times (sec) for each reagent addition, number of repetitions, and approximate total volumes used (ml/oligonucleotide/cycle) for each step in the synthetic cycle.

| Reagent | Time (sec) | Repetitions | Total Vol. ((1) |
|---|---|---|---|
| Deblock | 15 | 2 | 300 |
| Wash/Dry | 2 | | 190 |
| Couple phosphoramidite (+activator)* | 15 | | 190 |
| Wash/Dry | 2 | | 190 |
| Cap (A + a)** | 10 | | 190 |
| Wash/Dry | 2 | | 190 |
| Oxidize | 3 | | 190 |
| Wash/Dry | 2 | | 190 |

*Combined at a ratio of 1.8:1, activator to phosphoramidite.
**Combined at a ratio of 1:1, Cap A to Cap B.

In one embodiment of the method, when the synthesis of all oligonucleotides is complete, all of the tips are removed from the apparatus. Preferably, selected tips are removed as discussed below. The DNA products may then be cleaved from their supports and subjected to conventional deprotection as is known. If desired, the DNA products may also be further purified.

The chemistry of synthesizing DNA is well known and therefore will not be explained in detail. The general object of the deblocking operation at station 202 is to remove the 5' blocking elements from the derivatized nucleosides attached to the supports. Removal of the blocking elements enables the nucleosides to be reactive to the application of coupling reagents.

Once the deblocking step has been performed, all of the deblocked supports are washed and dried at station 204. This step ensures that all of the deblocking chemical reagent has been removed prior to performing the next step at station 206.

In a preferred method of synthesis, a selected tip is removed from the multi-pipette apparatus of the invention at station 214 as soon as the oligonucleotide associated with that tip is completed. This can be accomplished, for example, by the use of an ejector plate mounted in the lower surface of the apparatus, but above the tips and having a plurality of openings therethrough corresponding to the array of tips. In a typical holding plate, such as illustrated at 502 in FIG. 17, all of the openings, such as at 215, are smaller than the outer diameter of the upper rim 216 of the tips 46, but slightly larger than the outer diameter of the pipette shafts 218, so that all of the tips are ejected simultaneously upon lowering of the holder plate. However, in a preferred ejector plate (not shown) for selectively ejecting tips in accordance with this aspect of the invention, the openings are larger than the outer diameter of the upper rim of each tip. Mounted to each opening is a motorized closure device for bringing two opposed pins, plates, or other members together to partially close the opening in order to engage and eject a selected tip when the ejector plate is moved downward, but leaving clearance for the shaft of the pipette.

Figure 13A:
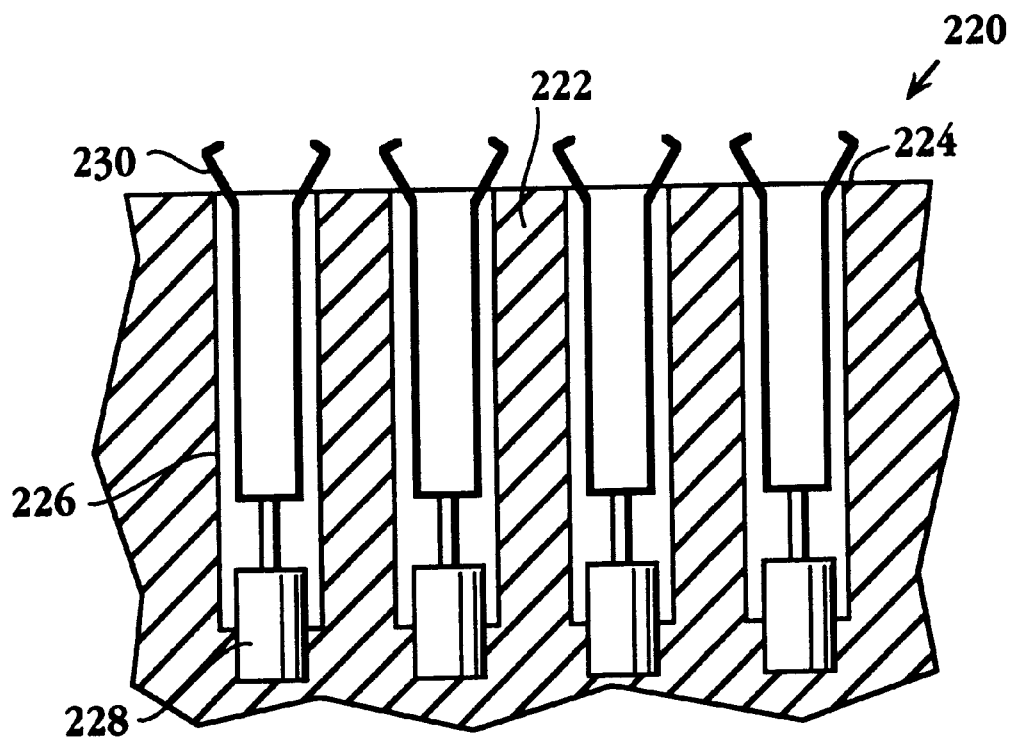
FIGS. 13A–13E illustrate tip removal by a tip puller.
Figure 13B:
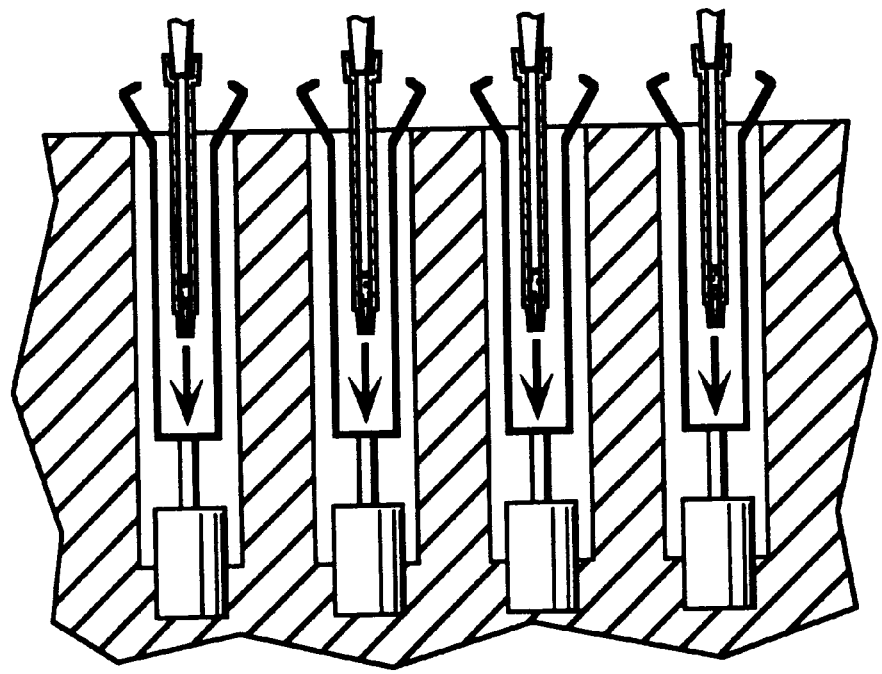
Figure 13C:
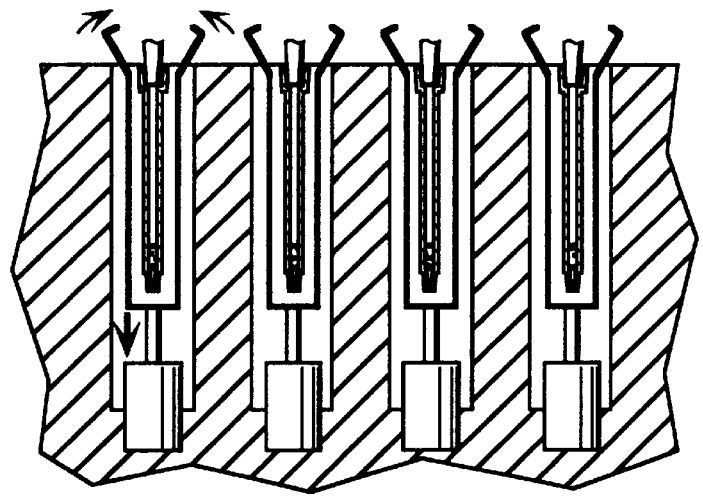
Figure 13D:
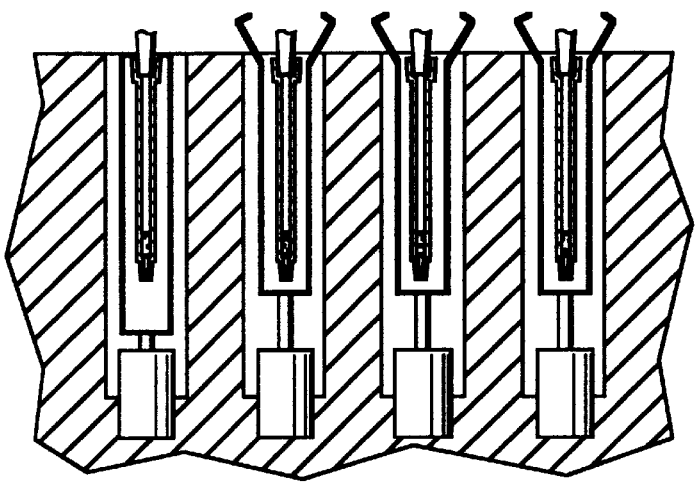
Figure 13E:
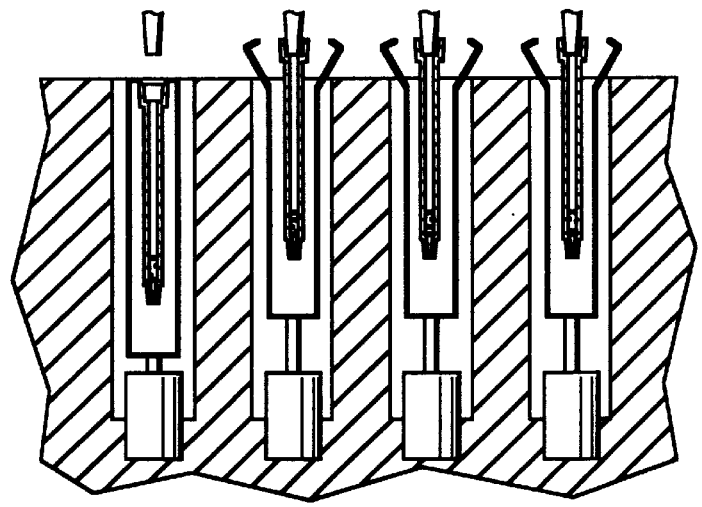

FIGS. 12 and 13A–13E illustrate an embodiment of a device for removing selected tips. The device 220 comprises a tip remover for use with a multi-channel apparatus such as shown at 100 and includes a housing 222 having a planar top surface 224 and having a plurality of elongated chambers, such as shown at 226, therein opening at said top surface and in alignment with the pipette shafts of the multi-channel apparatus. The chambers can be round, square or rectangular in cross section and are wide enough for receiving each of the tips when the apparatus 100 is moved into a position adjacent to the top of the tip remover (FIG. 13B). Each chamber has a clasping element for reversibly engaging a portion of selected tips. For example, the clasping element can be a plurality of opposed resilient fingers movable (e.g., by a solenoid such as shown at 228) between a retracted position and an extended position within each chamber 226. The device 220 includes a pair of opposed fingers 230,232 attached to a solenoid 228. The fingers can be formed of metal or plastic. In the extended position, the fingers are spread apart sufficiently for receiving a tip (FIG. 13B). In the retracted position, the fingers engage a portion of a tip, such as an annular upper rim 216 or flange (not shown) of a selected tip such that the selected tip is retained within the chamber of the device when the multi-channel apparatus is moved away (FIGS. 13B–13E). The fingers preferably have a distal hook or angled portion 234,236 for clasping the tips.

Once a selected tip has been removed from the apparatus, a new tip can be inserted at the vacant position. For example, new tips can be placed robotically into a box or rack which has an array of holes complementary to the fittings on the multi-channel apparatus. The apparatus is lowered onto the box in register with the array of holes in order to attach the new tips.

An advantage of this aspect of the present invention is the continuous mode of operation. The system operates in an infinite loop mode, performing the same cycle repeatedly as long as reagents are available. This contrasts with prior art instruments which are able to perform multiple syntheses (in a 96 well array) in a batch mode, but which must then be reloaded with an additional 96 tips in order to synthesize another batch. In a preferred embodiment of the present invention, once an oligonucleotide is completed on a solid support, the associated tip is detached from the multichannel apparatus, leaving available a space for a new tip, which can the be started on the next cycle, regardless of the completion status of any of it's neighbors. The method of the invention accomplishes this through the use of the phosphoramidite filling station, such as 162 or 184, which separates the only non-parallel aspect of oligonucleotide synthesis away from the rest of the cycle.

In a "uniformly filled plate," all of the wells contain the same reagent. As will be described hereinbelow, another embodiment of the present invention, which utilizes uniformly filled plates, comprises an apparatus having an array of pipettes (or syringes) which do not necessarily operate in unison, but where each pipette (or syringe) is under separate control of a controller so that each pipette (or syringe) can be manipulated independently of the other devices in the apparatus in order to aspirate or dispense reagent. In a preferred embodiment, the apparatus is provided with tips containing solid support therein, said tips arranged in alignment with the wells of a multi-well plate disposed beneath the apparatus.

In one embodiment of a controller, an apparatus such as at 100, but lacking plunger plate 120, includes a separate plunger drive system including a vertically mounted drive shaft such as described in U.S. Pat. No. 4,407,659, attached to each plunger (not shown).

Referring now to FIGS. 15–23, there is illustrated a multi-channel apparatus 300 according to another embodiment of a controller in this aspect of the invention. The apparatus is contained within housing 302 and includes cylinders 304, 306, 308, and 310, each having an upper end and a lower end defining a cylindrical chamber 312. As exemplified by cylinder 310, a plunger 314 is disposed within each cylinder for movement therein. The head of plunger 320 is retained within plunger plate 326 which engages rod 330 connected to actuating means (not shown), such as a motorized helical screw, for raising and lowering the plungers. Each plunger is sealed to the inner wall of its respective cylinder by means of a suitable seal, as for example an O-ring 332 (FIG. 12) in analogy with apparatus 100. At the lower end of each cylinder is a pipefting terminus. The terminus can be a tapered fitting (e.g., a Luer fitting), such as shown at 336, which is configured for detachably holding a fluid receptacle, such as a pipette tip 46. A passage in each tip holder such as at 338, is in fluid communication with the associated cylindrical chamber. Downward movement of plunger plate 326 via rod 330, lowers egress ports such as at 340, below each associated O-ring and provides a fluid flow path for the unidirectional introduction of fluid into the associated cylindrical chambers.

As seen in FIGS. 19–21, each cylinder is provided with four tabs extending radially from the outer surface of an upper portion and with a pair of pin members extending radially from the outer surface of a lower portion. As mounted in the apparatus, each barrel is rotatable about its central axis by an assembly 398 (FIG. 24) which includes a cylindrical rotating element 400 rotatably mounted within an annular cavity 402 and supported by annular ridge 406 within rigid support plate 404 (FIGS. 21,22,24–26). Radially extending recesses 410,412,414,416 are provided in the bottom surface of rotating element 400. The rotating element 400 can be a metallic or polymeric material. In the embodiment shown, annular gear 420 is mounted to the top surface of the rotating element 400 and is actuated electronically, for example by a switch 422 (mounted to cover plate 426) which unidirectionally rotates gear 420 in 90° increment (e.g., as shown by arrow 424). Switch 422, which is electrically connected to a control system (not shown), is mounted to cover plate 426 and includes a drive gear 428 in mesh with gear 420.

Figure 16:
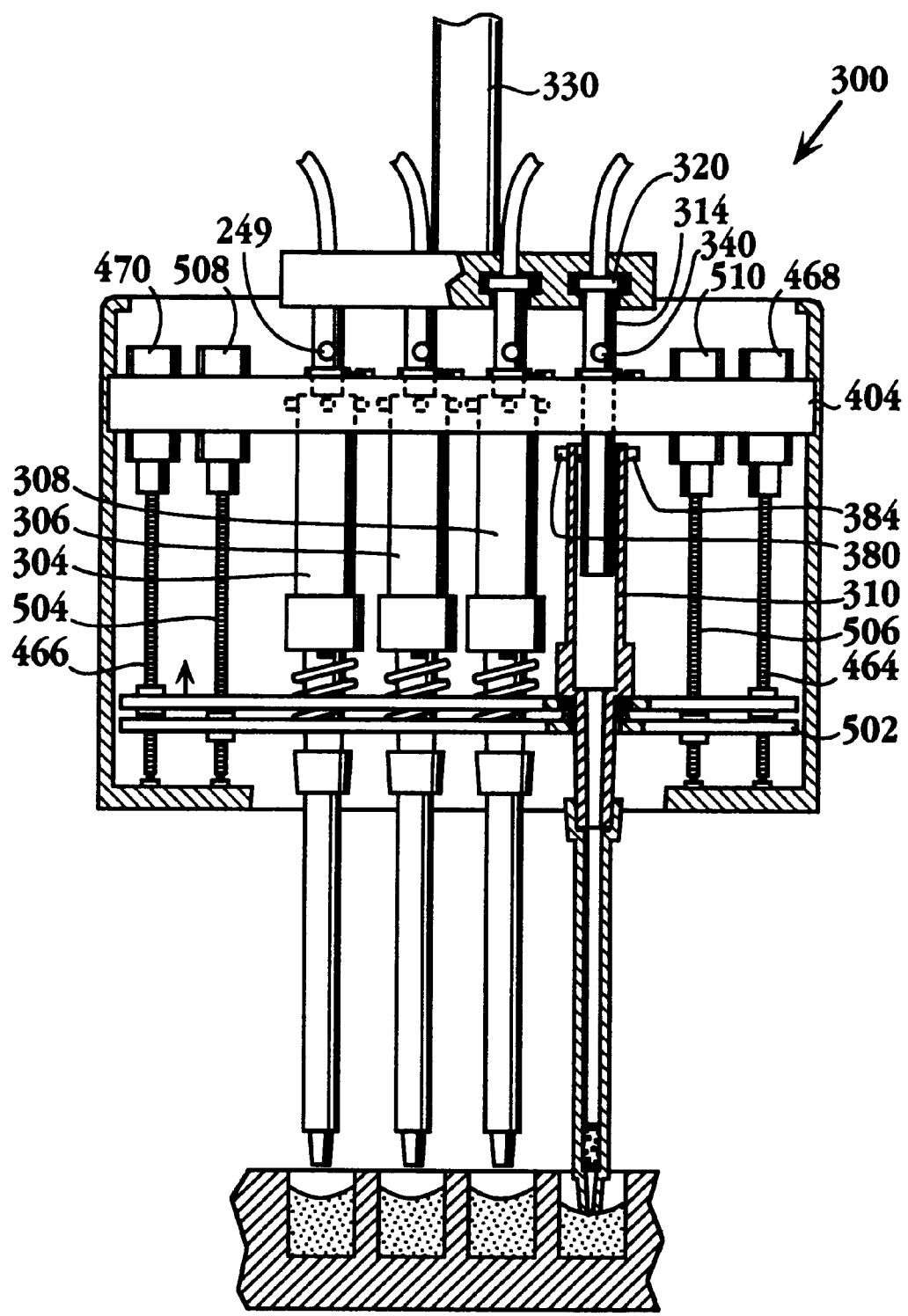
FIG. 16 is a partially cross-sectional view of the apparatus of FIG. 15 after lowering a selected tip.
Figure 17:
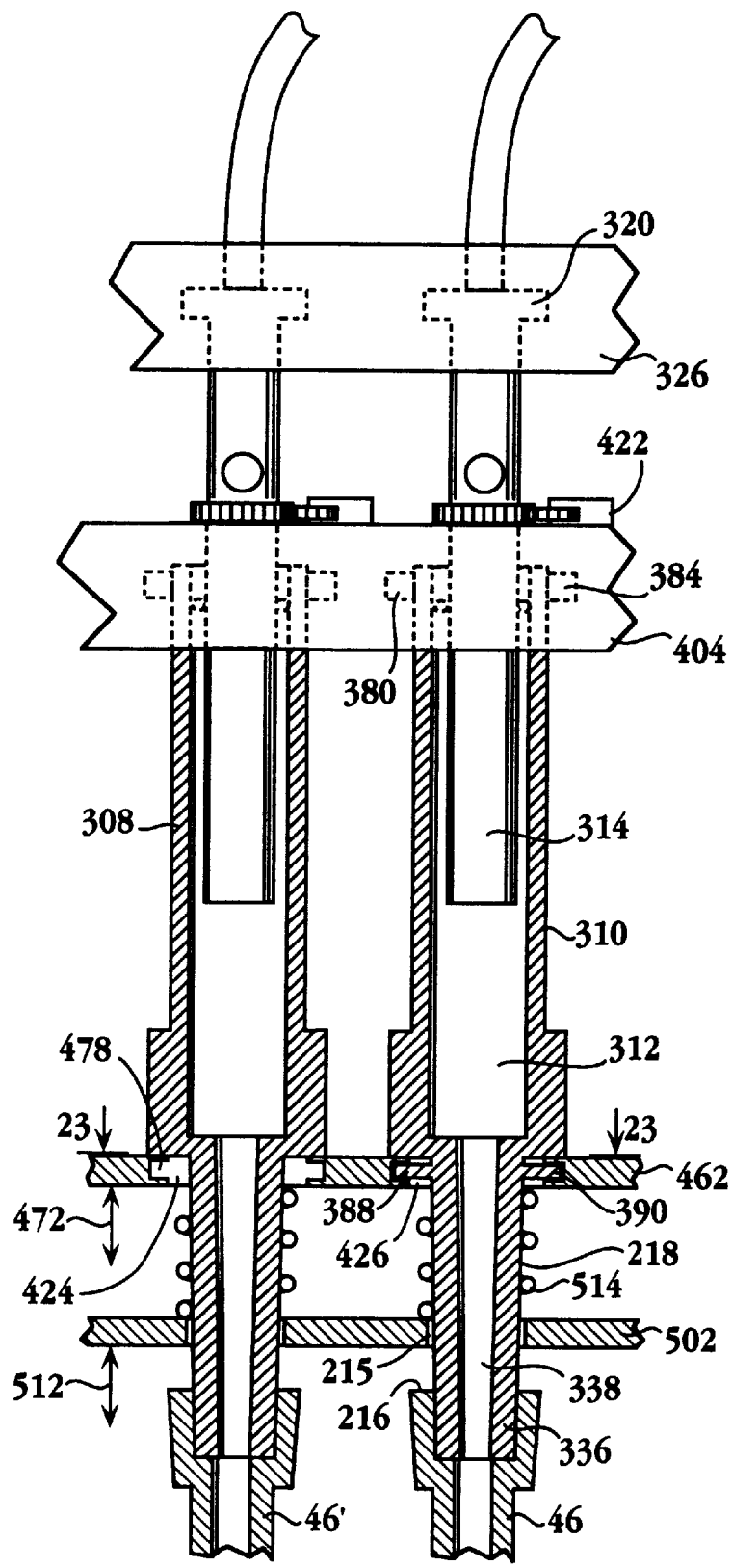
FIG. 17 is a partially cut away and enlarged view of the apparatus of FIG. 15.
Figure 18:
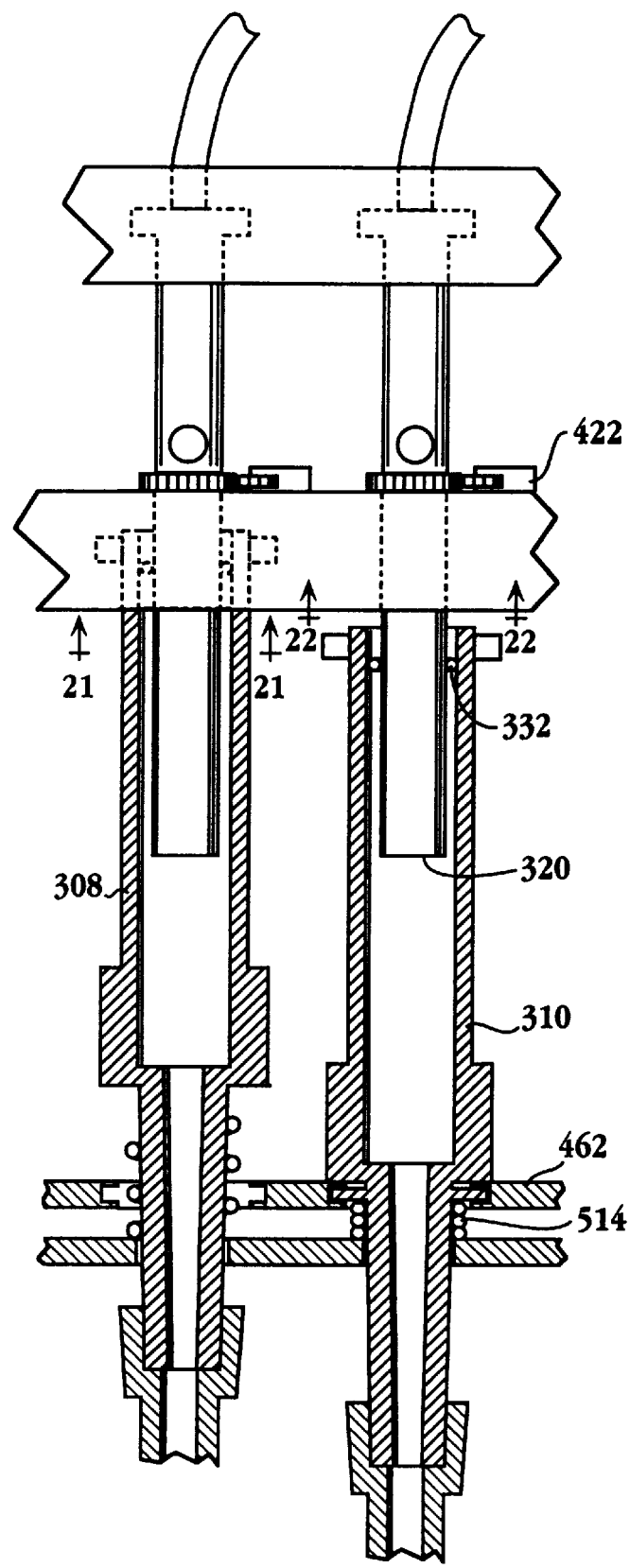
FIG. 18 is a partially cut away and enlarged view of the apparatus of FIG. 16.
Figure 24:
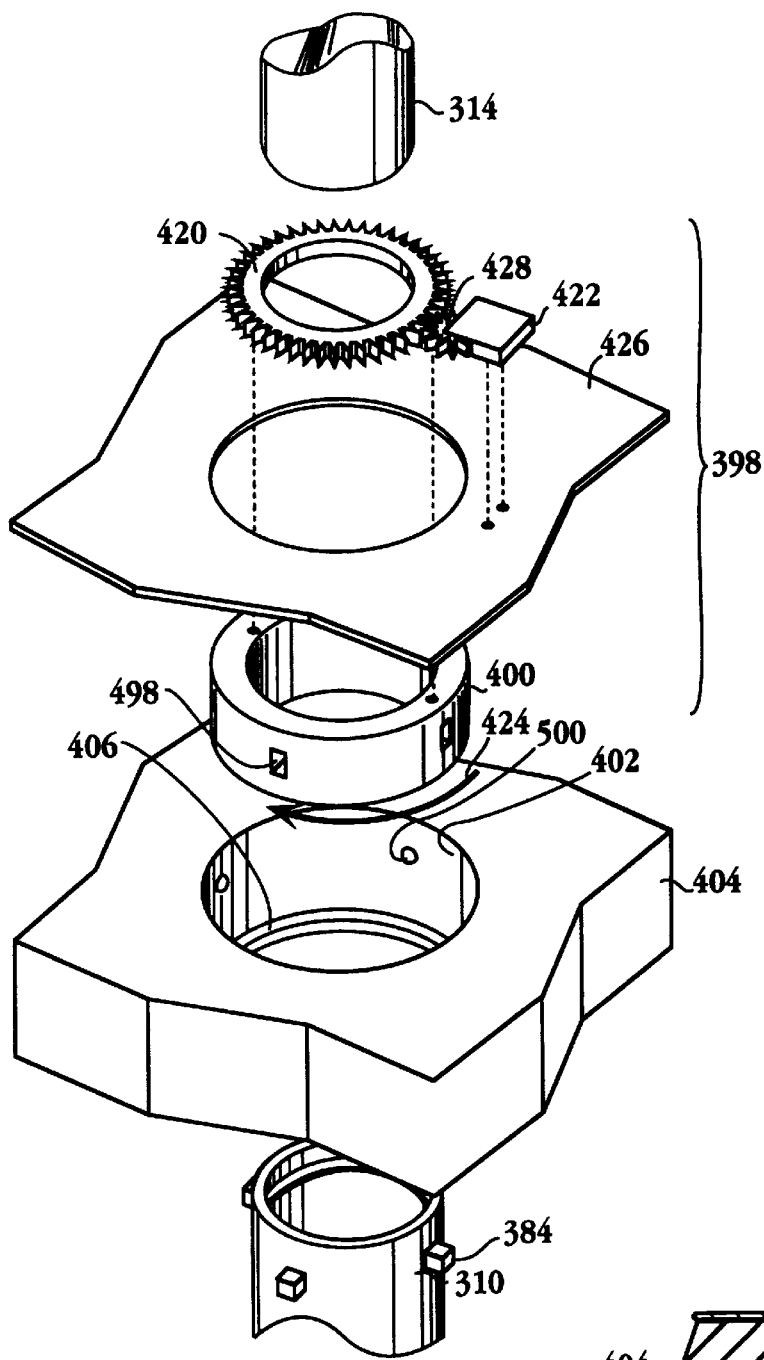
FIG. 24 illustrates an exploded perspective view of an embodiment of an assembly for rotating the barrels of the pipettes in the apparatus of FIG. 15.
Figure 25:
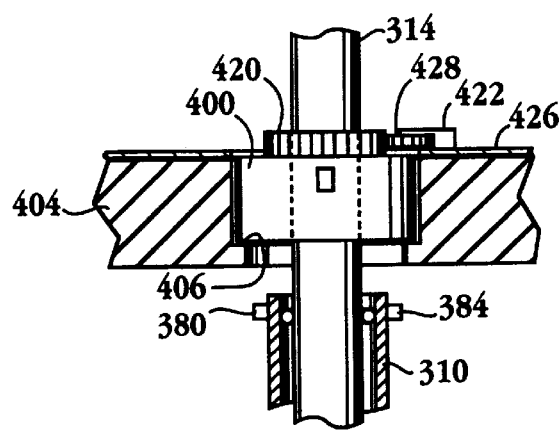
FIG. 25 is a partially cross-sectional side view of an assembly for rotating barrels of the pipettes in the apparatus of FIG. 15.
Figure 26:
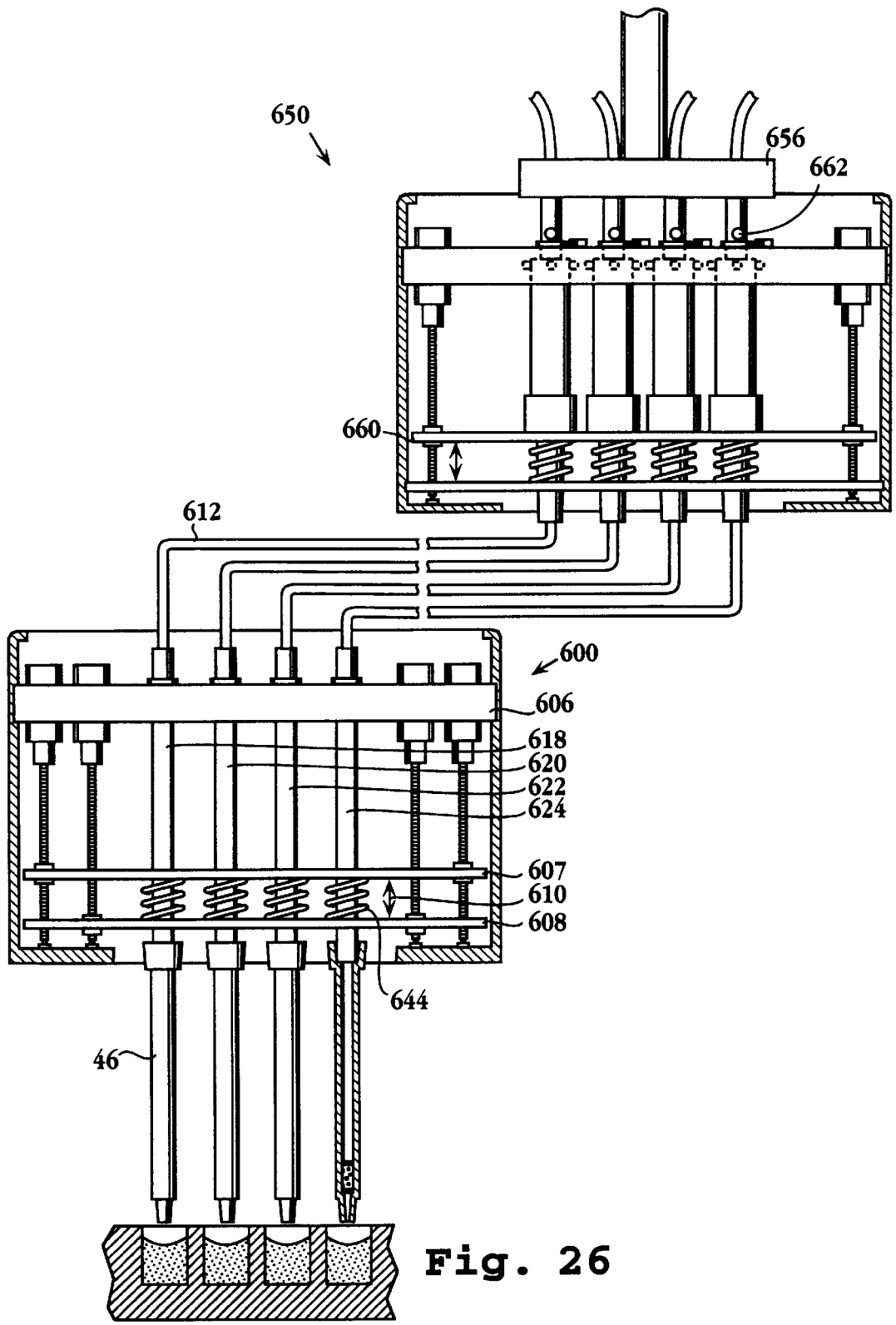
FIG. 26 illustrates a third embodiment of a multi-channel apparatus of the invention.
Figure 27:
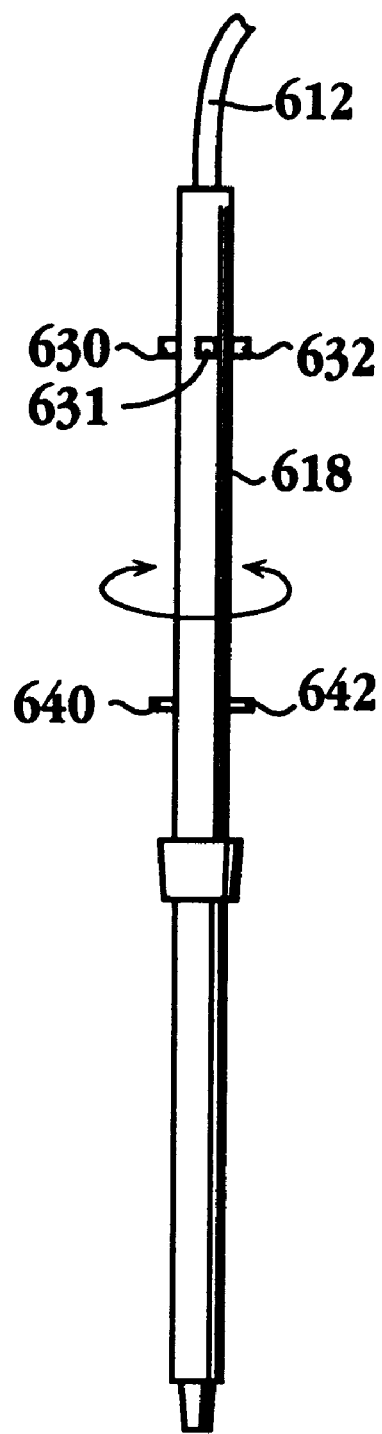
FIG. 27 is an enlarged view of a tube employed in the apparatus of FIG. 26.

Power plate 462 is mounted to helical screws 464 and 466 which are coordinately actuated by drive motors 468 and 470, respectively (FIG. 16). Rotation of said screws 464,466 causes vertical movement of said power plate 462 as indicated by double-headed arrow 472 (FIG. 17). The drive motors 468,470, in conjunction with the power plate 462, apply a drive force to the cylinders in the axial direction of the pipettes, as described hereinbelow. The drive motors are preferably stepper or incremental advance motors having a drive shaft or screw which moves axially in response to energization of the motor.

Figure 15:
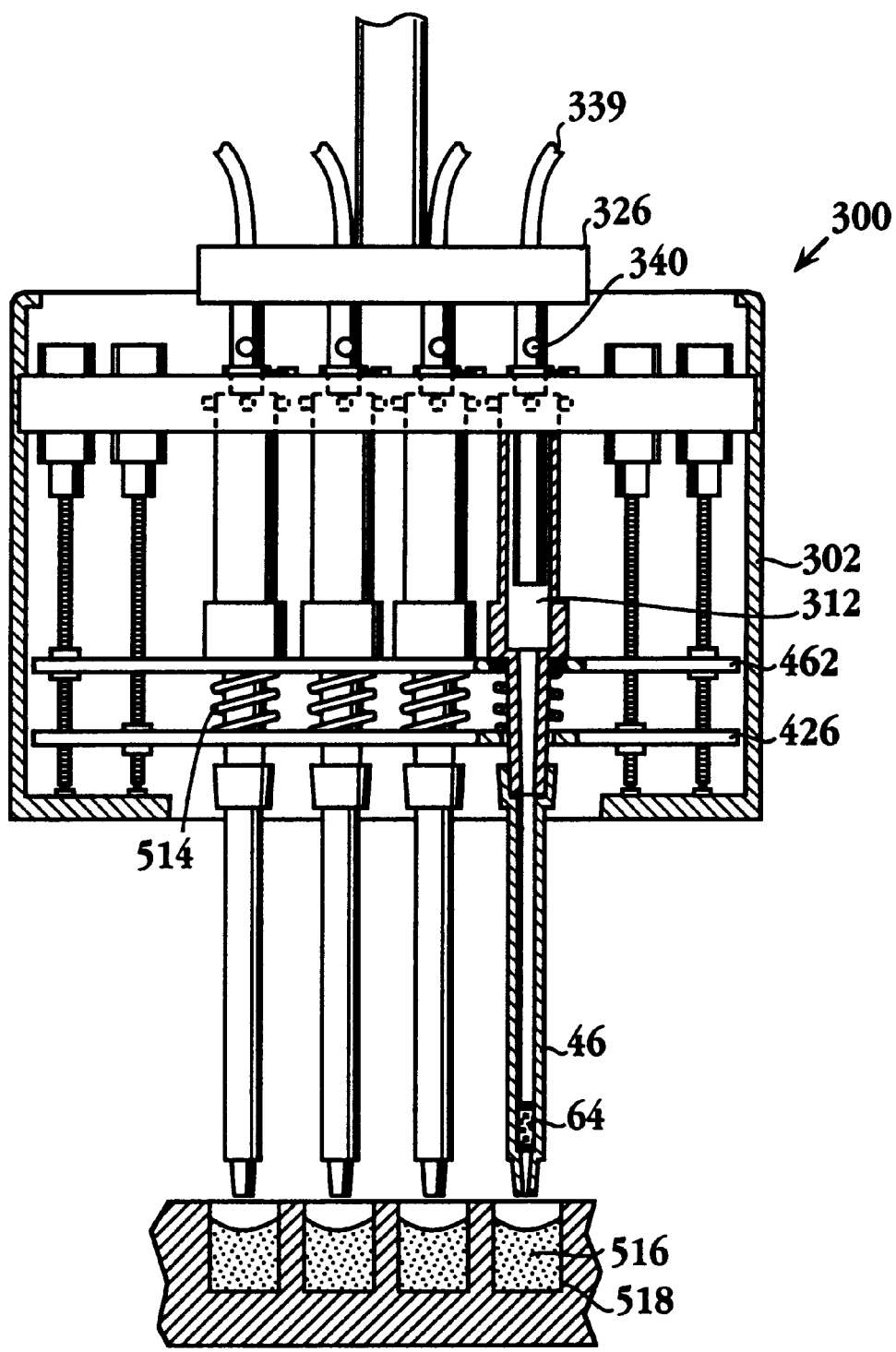
FIG. 15 is a partially cross-sectional view of a second embodiment of a multi-channel apparatus of the invention.

Each cylinder of the apparatus 300 extends through a circular opening, such as at 424,426, in power plate 462 (FIG. 15). The inner wall of each circular opening is provided with a horizontal annular recess, such as at 478 (FIG. 17). Each circular opening is also provided with a pair of opposed slots, such as at 484,486 for receiving said pin members, such as at 494,496 respectfully (FIG. 23).

The apparatus preferably incorporates a means for facilitating the alignment of the pin members 494,496 with slots 484,486 during rotational movement of the associated rotating element. For example, in one embodiment, rotating element 400 includes notches 498 positioned at 90° intervals around the side walls which interact with raised knobs or rollers 500 positioned at 90° intervals around the inner walls of cavity 402.

A rigid holding plate 502 is mounted to helical screws 504,506 which are coordinately activated by motors 508,510 respectively (FIG. 16). Rotation of said screws 504,506 causes either an elevation or a lowering of said holding plate as indicated by double-headed arrow 512. The lowering of said holding plate causes the release of tips such as tip 46.

Although other means for relatively moving such plates (e.g., gears and toothed rods) are known, the use of motorized screws advantageously provide precision needed to retain alignment of the array of tips with a corresponding multi-well plate. For two-dimensional arrays, such as 8 by 12, to be used with microtiter plates, the dimensions of the housing, holder plate, support plate, plunger plate and power plate are increased commensurately and can incorporate additional helical screw drive means.

In the embodiment of FIG. 17, coil springs, such as shown at 514, surrounding the lower end of each cylinder and interposed between the associated pin members and the top surface of the holding plate 502, normally urge said cylinder upwardly. Referring to cylinder 310, tabs 380,382,384,386 normally are disposed within corresponding radially extending recesses 410,412,414,416 in the bottom surface of a rotating element 400 (FIGS. 21 and 22).

In use, the apparatus allows aspiration and expulsion of liquid reagent into selected tips arranged in an array. When it is desired to aspirate liquid into selected tips, each cylinder is rotated to either a "locked" or an "unlocked" position for engagement with the power plate 462. As illustrated by reference to cylinder 308 (FIGS. 17,18,23) in an "unlocked"

position, pin members 494,496 are aligned with slots 484, 486 and lowering of power plate 462 does not affect the position of the unlocked cylinder.

In a "locked" position, as exemplified by cylinder 310 (FIG. 23), the pin members 388,390 are offset, preferably by 90°, from slots 488,490, and lowering of power plate 462 causes lowering of the locked cylinders only. The relative movement of a plunger and the associated cylinder selectively lowers the attached tip to a position for contacting the liquid 516 in the selected well 518 and generates suction in chamber 312 which causes aspiration of liquid reagent into the tip 46 for contacting solid support matrix 64 retained therein.

In another embodiment of the invention (FIG. 26,27), apparatus 600 comprises an array of rigid hollow tubes as at 618, 620, 622, 624 mounted within a housing (not shown) in analogy with the apparatus 300. Each tube such as 618 is provided with tabs such as at 630–633, pin members such as 640,642, and a helical spring 644 in analogy with the cylinders of device 300. Each tube is engaged with a fixed support plate 606, a power plate 607 and a holder plate 608. Support plate 606 contains rotating elements 300. Each tube is separately movable vertically as indicated by double-headed arrow 610. However each tube does not contain a plunger, but is connected to tubing 612 at an upper end. The tubes 612 are connected to a suction means, such as a multi-channel apparatus 650 for selectively applying a partial vacuum to a selected tube within the array. Apparatus 650 is analogous to apparatus 300 except that the holding plate is not vertically movable. In operation, in order to aspirate from selected wells or vessels in a container (e.g., a microtiter plate) disposed beneath apparatus 600, selected tubes are "locked", in analogy with the cylinder of apparatus 300. Simultaneously, the associated cylinders in apparatus 650 are locked. Downward vertical movement of the power plate 607 causes downward movement only of locked tubes to contact liquid in said selected wells. Simultaneous downward vertical movement of power plate 660 causes downward movement only of locked cylinders to cause suction in the associated tubes for aspirating liquid from said selected wells.

In a procedure for washing or drying a solid support retained in attached pipette tips 46, downward movement of plunger plate 656, lowers egress ports such as at 662, below each associated O-ring (not shown) and provides a flow path for the unidirectional introduction of fluid into the cylindrical chambers.

Figure 28:
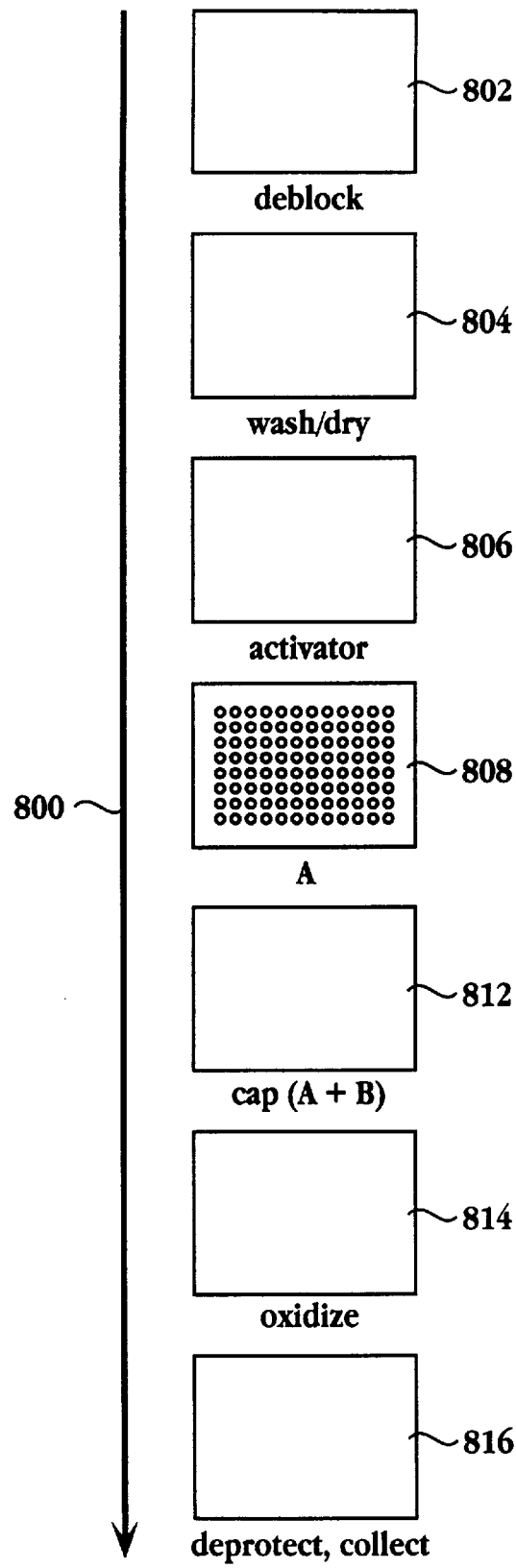
FIG. 28 is a schematic diagram of a layout of a series of reagent stations for use in oligonucleotide synthesis.

FIG. 28 schematically illustrates an arrangement of troughs (represented by rectangles) and uniformly filled multi-well plates containing reagents for oligonucleotide synthesis by a computer controlled bench-top system equipped with an overhead multi-channel pipette apparatus (e.g., apparatus 300) capable of independent selectable aspiration and delivery of liquids from each well.

Uniformly filled plates are readily prepared, for example using a robot system having a conventional multi-channel pipette apparatus, and transferring from a trough or other compatible reagent container to the plate. A preferred method for filling uniformly filled plates utilizes an apparatus such as at 162 incorporating a manifold fed from freshly prepared reagents.

In the operation of this aspect of the invention, for each base to be added to a growing chain, the pipette apparatus proceeds through different stations generally along the direction indicated by arrow 800 (FIG. 28). A synthetic cycle for the addition of each nucleotide begins at station 802 which contains deblocking chemical. Station 804 is an area for performing a washing and drying procedure; station 806 contains activator; station 808 comprises a uniformly filled plate containing reagent coupling agent (i.e., phosphoramidite (A in the example shown)); station 810 contains acetonitrile; station 812 contains reagent capping chemical; station 814 contains reagent oxidizing chemical. The apparatus returns to station 802 to repeat the cycle if other phosphoramidites are to be added to a growing chain. A fresh uniformly filled plate containing selected phosphoramidite to be newly added is provided at station 808 during each cycle. A station for deprotection and collection of product is indicated at 816 at which completed tips can be removed selectively as described hereinabove.

In a preferred method, after each reactive step, the apparatus is positioned at station 804 and the solid supports are washed unidirectionally with solvent and then dried by inert gas.

An advantage of this aspect of the invention is the continuous mode of operation. The system operates in an infinite loop mode, performing the same cycle repeatedly as long as reagents are available. This contrasts with prior art instruments which are able to perform multiple syntheses (in a 96 well array) in a batch mode, but which must then be reloaded with an additional 96 tips in order to synthesize another batch. In a preferred embodiment of the present invention, once an oligonucleotide is completed on a solid support, the associated tip is detached selectively from the multichannel apparatus, leaving available a space for a new tip, which can then be started on the next cycle, regardless of the completion status of any of it's neighbors.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

We claim:

1. A pipetting device for solid phase synthesis, said device comprising a cylinder having an upper end and a lower end and defining a cylindrical chamber extending therebetween, a plunger having an upper end and a lower end, wherein the plunger (i) is slidably movable in the cylindrical chamber between a retracted and an inserted position, (ii) has an outer diameter that is less than the inner diameter of the chamber, and wherein the difference between the outer diameter of the plunger and the inner diameter of the cylindrical chamber is large enough to allow fluid passage and (iii) has a central passageway leading from a portion of the plunger above said chamber to an egress port which traverses a lateral wall of the plunger within said chamber, a seal disposed adjacent the upper end of said cylinder for holding said plunger during movement thereof, and a pipetting terminus for mounting a disposable pipette tip, wherein said plunger is movable between (i) a retracted position wherein said egress port is positioned above said chamber, and (ii) an inserted position wherein said egress port is positioned within said chamber, for introducing a fluid through said passageway into the cylindrical chamber for delivery to a pipette tip when a pipette tip is mounted on said pipetting terminus.

2. The device of claim 1, which further includes a pipette tip mounted on said pipetting terminus, and said pipette tip contains a solid support for solid phase synthesis.

3. The device of claim 2, wherein said solid support contains at least one blocked protected nucleoside attached covalently thereto.

4. The device of claim 2, wherein said solid support contains at least one protected amino acid residue attached covalently thereto.

5. An apparatus for solid phase synthesis, said apparatus comprising:

a plurality of devices in accordance with claim 1, wherein the plungers of said devices are operatively attached to a plunger plate for simultaneously moving the plungers relative to said cylindrical chambers for liquid dispensing.

6. An apparatus for solid phase synthesis, said apparatus comprising:

a plurality of devices in accordance with claim 2, wherein the plungers of said devices are operatively attached to a plunger plate for simultaneously moving the plungers relative to said cylindrical chambers for liquid dispensing.

7. An apparatus for solid phase synthesis, said apparatus comprising:

a plurality of devices in accordance with claim 1, wherein the movement of each device is under separate control of a controller so that each said devices can be manipulated independently of the other devices in the apparatus.

8. The apparatus of claim 7, which further includes:

a power plate for moving the cylinder(s) of one or more of said devices longitudinally, said plate further defining apertures through which the cylinders protrude, and locking means associated with each cylinder for reversibly and separately locking each cylinder to said power plate.

9. The apparatus of claim 8, wherein each cylinder includes one or more pin members for locking with the power plate, the power plate includes corresponding recesses for allowing said pin members to traverse the power plate for each cylinder that is in an unlocked position, and the apparatus further includes means for independently rotating each cylinder about its longitudinal axis so that said pin member(s) may be locked to or unlocked from the power plate.

10. The apparatus of claim 7, which further includes a plurality of drive motors each having a drive shaft connected to anassociated plunger for independent longitudinal movement of each plunger.

* * * * *